United States Patent [19]

Aviv et al.

[11] Patent Number: 5,256,546
[45] Date of Patent: * Oct. 26, 1993

[54] BACTERIAL EXPRESSION OF PORCINE GROWTH HORMONE

[75] Inventors: Haim Aviv; Marian Gorecki, both of Rehovot; Avigdor Levanon, Netania; Amos Oppenheim, Jerusalem; Tikva Vogel, Rehovot; Elisha Zeelon, Hashiva; Menachem Zeevi, Ramat Gan, all of Israel

[73] Assignee: Bio-Technology General Corp., New York, N.Y.

[*] Notice: The portion of the term of this patent subsequent to Jun. 30, 2009 has been disclaimed.

[21] Appl. No.: 840,579

[22] Filed: Feb. 24, 1992

Related U.S. Application Data

[63] Continuation of Ser. No. 388,010, Jul. 31, 1989, abandoned, which is a continuation of Ser. No. 821,830, Jan. 23, 1986, abandoned, which is a continuation-in-part of Ser. No. 514,188, Jul. 15, 1983, abandoned.

[51] Int. Cl.$^5$ .................... C12P 21/02; C12N 15/18; C12N 15/73; C12N 15/03
[52] U.S. Cl. .................... 435/69.4; 435/252.33; 435/320.1
[58] Field of Search .............. 435/69.4, 91, 172.3, 435/252.3–252.35, 320.1; 536/27, 23, 51; 935/9, 13, 29, 43, 45, 47, 48, 61, 72, 73

[56] References Cited

U.S. PATENT DOCUMENTS 4,578,355  3/1986  Rosenberg .................... 435/320
5,126,252  6/1992  Oppenheim et al. .............. 435/69.4

OTHER PUBLICATIONS

Rosenberg et al; Methods in Enzymology 101: 123 (1983).
Seeberg et al; DNA 2: 37 (1983).
Movva et al; Chem. Abstr. 101: 18489e (1984).

Primary Examiner—James Martinell
Attorney, Agent, or Firm—John P. White

[57] ABSTRACT

A plasmid for the production of porcine growth hormone or an analog thereof which upon introduction into a suitable bacterial host containing the thermolabile repressor $C_I$ renders the host cell capable, upon increasing the temperature of the host cell to a temperature at which the repressor is destroyed, of effecting expression of DNA encoding porcine growth hormone and production of porcine growth hormone or analogs thereof. The plasmid is a double-stranded DNA molecule which includes in 5' to 3' the following: a DNA sequence which contains the promoter and operator PLOL from lambda bacteriophage; the N utilization site for binding antiterminator N protein produced by the host cell; a DNA sequence which contains a ribosomal binding site for rendering the mRNA of the gene encoding porcine growth hormone capable of binding to ribosomes within the host cell; an ATG initiation codon; a restriction enzyme site for inserting the gene encoding porcine growth hormone into the plasmid in phase with the ATG initiation codon; a gene encoding porcine growth hormone; and additionally a DNA sequence which contains an origin of replication from a bacterial plasmid capable of autonomous replication in the host cell and a DNA sequence which contains a gene associated with a selectable or identifiable trait which is manifested when the plasmid is present in the host cell.

12 Claims, 12 Drawing Sheets

BACTERIAL EXPRESSION OF PORCINE GROWTH HORMONE

This is a continuation of application Ser. No. 388,010, filed Jul. 31, 1989, now abandoned, which is a continuation of U.S. Ser. No. 821,830, filed Jan. 23, 1986, now abandoned, which was a continuation-in-part of U.S. Ser. No. 514,188, filed Jul. 15, 1983, now abandoned, the contents of each of which are hereby incorporated by reference.

BACKGROUND OF THE INVENTION

One aspect of genetic engineering involves the insertion of foreign DNA sequences derived from eukaryotic sources into *Escherichia coli* or other microorganisms. A further refinement of genetic engineering concerns inducing the resulting microorganism to produce polypeptides encoded by the foreign DNA. Production of polypeptides can be considered a two-step process, with each step including numerous substeps. The two steps are transcription and translation. To produce a polypeptide efficiently and in quantity both steps of the process must be efficient. Transcription is the production of mRNA from the gene (DNA). Translation is the production of polypeptide from the mRNA.

A critical substep of the transcription process is initiation, that is, the binding of RNA polymerase to a promoter-operator region. The sequence of deoxyribonucleotide bases which make up the promoter region may vary and thereby affect the relative efficiency of the promoter. The efficiency depends on the affinity of the RNA polymerase for the promoter.

The efficiency of translation is affected by the stability of the mRNA. Increased stability of the mRNA permits improved translation. Although the exact determinants of mRNA stability are not precisely known, it is known that mRNA secondary structure as determined by the sequence of its bases has a role in stability.

The initial substep of translation involves binding of the ribosome to a base sequence on the mRNA known as the Shine-Dalgarno sequence or the ribosomal binding site (RBS). The synthesis of polypeptides begins when the ribosome migrates along the mRNA to the AUG start codon for translation. Generally these codons are found approximately 10 bases "downstream" from the Shine-Dalgarno site. Factors which increase the efficiency of translation include those which enhance binding of the ribosomes to the Shine-Dalgarno site. It has been shown that the secondary structure of the mRNA in the region of the Shine-Dalgarno sequence and the AUG codon and the distance between the Shine-Dalgarno sequence and the AUG codon each play a critical role in determining the efficiency of translation. Other factors which affect the efficiency of translation are premature termination and attenuation. Efficiency of translation can be improved by removing the attenuation sites.

A difficulty encountered in attempts to produce high amounts of eukaryotic polypeptides in bacterial cells involves the inability of cells producing large amounts of mRNA to grow efficiently. This difficulty can be eliminated by preventing transcription by a process known as repression. In repression genes are switched off due to the action of a protein inhibitor (repressor protein) which prevents transcription by binding to the operator region. After microorganisms have grown to desired cell densities, the repressed genes are activated by destruction of the repressor or by addition of molecules known as inducers which overcome the effect of the repressor. Numerous reports may be found in the literature concerning the cloning of eucaryotic genes in plasmids containing the $P_L$ promoter from bacteriophage. (Bernard, H. V. et al., Gene (1979) 5, 59; Derom, C. et al., Gene (1982) 17, 45; Gheysen, D. et al., Gene (1982) 17, 55; Hedgpeth, J. et al., Mol. Gen. Genet. (1978) 163, 197; Remaut, E. et al., (1981) Gene 15, 81; and Derynck, R., et al., Nature (1980) 287, 193. In addition, European Patent Application No. 041.767, published Dec. 16, 1981 describes expression vectors containing the $P_L$ promoter from λ bacteriophage. However, none of these references describe the use of the $C_{II}$ ribosomal binding site.

The use of a vector containing the $P_L$ promoter from bacteriophage and the $C_{II}$ ribosomal binding site has been described. (Oppenheim, A.B. et al., J. Mol. Biol. (1982) 158, 327 and Shimatake, H. and Rosenberg, M., Nature (1981) 292, 128.) These publications describe the production of increased levels of $C_{II}$ protein but do not involve or describe the production of eucaryotic proteins.

In 1982 Shatzman and Rosenberg presented a poster at the 14th Miami Winter Symposium (Shatzman, A. R. and Rosenberg, M., 14 Miami Winter Symposium, abstract p98 [1982]). This abstract provides a non-enabling disclosure of the use of a vector containing $P_L$ from λ bacteriophage, Nut and the $C_{II}$ ribosomal binding site to synthesize a "eucaryotic" polypeptide (SV40 small T antigen is actually not a eucaryotic polypeptide but a viral protein) in an amount greater than 5% of the cell protein in an unnamed bacterial host. The operator used is not defined. Neither an origin of replication nor a gene for a selectable phenotype is identified. This system with which the vector is used is described as including certain host lysogens into which the vector can be stably transformed. The present invention in one embodiment, i.e., pMG100, may have certain similarities to this vector. However, it is not transformed into a host lysogen, but rather into suitable *E. coli* host strains which contain the thermolabile repressor $C_I$ and the N gene but from which the rest of the lysogen has been removed. Moreover, it has been employed to produce bGH and hGH analogs in amounts in excess of 20% of total cell protein.

In addition, in other embodiments of this invention ribosomal binding sites which differ from $C_{II}$ are employed. Also, in the presently most preferred vectors, pND5 and its derivatives, nonessential sequences have been removed to create a vector permitting polypeptide production in amounts which are more than 10% greater than those obtained with pMG100.

Recently, applicants have learned of the existence of a pending U.S. patent application in the name of M. Rosenberg filed under Ser. No. 457,352 by the National Institutes of Health, Dept. of Health and Human Services, U.S.A. Portions of this application have been obtained from the National Technical Information Service, U.S. Dept. of Commerce. However, the claims are not available and are maintained in confidence. The available portions of the application have been reviewed. It indicates that the host is important (p8, line 17) but fails to identify any suitable host. It further depends upon the use of a λ mutant which is not specified (p4, line 20). It indicates that the host contains lysogens (p8, line 18) unlike the present invention in which the host is not lysogenic. It mentions cloning and expression of a eucaryotic gene, monkey metallothionein gene, (p7, line 18) but does not provide details It specifies that neither the sequence nor the position of any nucleotide in the $C_{II}$ ribosomal binding region has been altered (p. 3, line 27) In the present invention such alteration is possible No disclosure is present in the art concerning: successful expression with a $P_L$-$C_{II}$ containing vector system of bovine or human growth or hormones; production of bGH or hGH analogs having biological activity; compositions containing such analogs or uses of them; or induction methods for achieving polypeptide production in amounts greater than 20% of the total protein produced by the host.

The only disclosure in the art concerning production of bGH analogs by hosts transformed with genetically engineered vectors involves the use of the Trp promoter to produce a bGH analog having the amino acid Met at the N-terminus of the phenylalanine form of natural bGH (P. H. Seeburg et al., DNA 2:37 (1983)).

The only disclosure in the art concerning production of hGH analogs by hosts transformed with genetically engineered vectors involves the use of the Lac and Trps promoters to produce an analog of hGH having the amino acid Met at the N-terminus of the natural hGH. (D. V. Goedell et al., Nature 281:544 (1979)).

Pituitary derived porcine growth hormone has been partially purified (H. Chen et al., J. Biol. Chem. 245:3402 (1970)) and partially sequenced (Mills et al., J. Biol. Chem. 245:3407 (1970)). The effects of injection of pituitary derived pGH on porcine have been studied (L. J. Machlin, J. Anim. Sci. 35:794 (1972)), E. J. Turman and F. M. Andrews, J. Anim. Sci. 14:7 (1955), B. Henricson and S. Ullberg, J. Anim Sci. 119:1002 (1960), and H. Papkoff et al., Arch. Biochem. and Biophys. 96:216 (1962)). P. H. Seeberg et al. (DNA 2:37 (1983)) describe the production of a Met-pGH analog under the control of a Trp promoter.

The present invention relates to expression plasmids which produce porcine growth hormone (pGH) or analogs thereof as well as to a method for producing pGH or an analog thereof in bacteria utilizing these plasmids. The present invention also relates to compositions containing such pGH or an analog thereof and the use of pGH or analogs to increase milk or meat production in porcines or to alter the carcass compositions of porcines.

SUMMARY OF THE INVENTION

This invention concerns a plasmid for production of porcine growth hormone or an analog thereof which upon introduction into a suitable bacterial host cell containing the thermolabile repressor $C_I$ renders the host cell capable, upon increasing the temperature of the host cell to a temperature at which the repressor is destroyed, of effecting expression of DNA encoding porcine growth hormone and production of porcine growth hormone or analog thereof comprising:

a double-stranded DNA molecule which comprises in 5' to 3' order the following:

a DNA sequence which contains the promoter and operator $P_LO_L$ from lambda bacteriophage;

the N utilization site for binding antiterminator N protein produced by the host cell;

a DNA sequence which contains a ribosomal binding site for rendering the mRNA of the gene encoding porcine growth hormone capable of binding to ribosomes within the host cell;

an ATG initiation codon;

a restriction enzyme site for inserting the gene encoding porcine growth hormone into the plasmid in phase with the ATG initiation codon; and a gene encoding porcine growth hormone;

and which additionally includes a DNA sequence which contains an origin of replication from a bacterial plasmid capable of autonomous replication in the host cell and a DNA sequence which contains a gene associated with a selectable or identifiable phenotypic trait which is manifested when the plasmid is present in the host cell. Preferred plasmids include pRec pig 24, p6200, p3007 p4005 and p515. Plasmid pRec pig 24 is especially preferred and has been deposited with the American Type Culture Collection (ATCC) under Accession No. 53433. Plasmid p6200 has been deposited with the American Type Culture Collection (ATCC) under Accession No. 39980.

The plasmids of this invention can be introduced into suitable hosts where the gene encoding porcine growth hormone can be expressed and the porcine growth hormone or analog thereof produced. Suitable hosts include *Escherichia coli* A1637, A1645, A2602, A1563 and A2097; A1645 and A2097 being presently preferred.

A1637 was obtained from c600 by inserting transposon containing tetracycline resistance gene within the galactose operon as well as the lambda system for expression which is close to galactose operon. c600 is available from the American Type Culture Collection as ATCC Accession No. 23764.

A1645 was obtained from A1637 by selection for Gal+ (ability to ferment galactose) as well as loss of tetracycline resistance. It still contains the lambda expression system but part of the transposon has been removed by selection. Its phenotype is c600 r⁻m+ gal⁺ thr⁻ leu⁻ Z⁻ (λcI857ΔH1ΔBam N+).

Both A1637 and A1645 have been deposited with the American Type Culture Collection in Rockville, Maryland, U.S.A. containing various plasmids as described more fully hereinafter. All such deposits were made pursuant to the Budapest Treaty on the International Recognition of the Deposit of Microorganisms.

A2097 is derived from A1645. Its phenotype is A1645 lacΔXA21 proC::Tn10.

A2602 and A1563 are derived from SA500. Their phenotypes are SA500 his⁻ilu⁻gal⁺Δ8(λCI857ΔH1 ΔBAM N+⁻ and SA500 his⁻ ilu⁻ gal⁺ Δ8 lac ZxA21 CI857 int2 xisl nutL3 ΔH1), respectively. SA is available from the ATCC as ATCC Accession No. 15746.

Prototrophic *E. coli* may also be used as hosts for this invention. A preferred prototrophic host is *E. coli* A4255. Strain A4255 containing the plasmid pRec pig 24 has been deposited with the American Type Culture Collection (ATCC) under ATCC Accession No. 53433.

The resulting host vector systems can be employed to manufacture porcine growth hormone or analogs thereof. The host cells containing the plasmids are grown under suitable conditions permitting production of porcine growth hormone or analog thereof which is then recovered. Presently preferred conditions for growth of p3007 in A1645 and pRec pig 24 in A2097 is initial growth at 30° C. and then continued growth at 42° C. for about 120 minutes. The presently preferred growth media for p3007 in A1645 and pRec pig 24 in A2097 is casein hydrolysate. Presently preferred growth conditions for growth of pRec pig 24 in A4255 is growth at 30° C., continued growth at 42° C. for 15 minutes, and then further at 38° C. for 120 minutes. The preferred growth media for pRec pig 24 in A4255 is the minimal media described in Example 9. Production of met-asp-gln pGH by pRec pig 24 in minimal growth media is preferred.

Using the host vector systems, porcine growth hormone analogs have been prepared. The analogs may be incorporated into veterinary compositions. They may be used directly, or in such compositions to stimulate milk or meat production in porcines or to alter the carcass composition of porcines.

BRIEF DESCRIPTION OF THE FIGURES

The restriction maps for each of the plasmids shown in FIGS. 1-12 do not identify all the restriction sites present on each plasmid. In some cases restriction sites are shown in one Figure but not in another. However, in all cases those restriction sites necessary for a complete understanding of the invention are shown.

FIG. 1A. This plasmid was built by inserting a fragment of λ phage DNA contained between restriction sites HaeIII (location 38150) and Sau3a (location 38362) into a pKC30 plasmid DNA cleaved with Hpa1 and BamH1. The HaeIII-Sau3a fragment carries $nut_R$, $t_{R1}$, $cy^-$ and ribosomal binding site of $C_{II}$ protein ($C_{II}$-RBS). Subcloning of the $C_{II}$-RBS containing DNA into pKC30 creates pMG100 which contains a unique BamH1 restriction site right after the ATG initiation codon of $C_{II}$-RBS and an NdeI restriction site within the ATG triplet (FIG. 1B). Numbers in parentheses denote location of restriction sites on the λ phage DNA.

```
GGAATTCC

CCTTAAGG
``` was attached by ligation. The product was cleaved with EcoR1 and inserted into pBR322 which had been cleaved with EcoR1. A clone, pALR1, was isolated which upon cleavage with EcoR1 released a 1200 pb fragment with the sequence:

```
AATTCCCA...
    GGGT...
``` at the 5' end. Formation of this sequence demonstrates that pALR1 contains an EcoR1 restriction site directly adjacent the TTC codon for residue number 1 (phenylalanine) of authentic bGH. pALR1 was subjected to a partial cleavage with Pst1. The digest was ligated with HindIII linkers and cleaved with EcoR1 and HindIII. The fragment containing bGH cDNA was isolated and subcloned into pBR322 between EcoR1 and HindIII restriction sites to give pAL500. The subcloned bGH cDNA fragment was then excised from pAL500 with EcoR1 and HindIII, "filled in" with DNA polymerase "Klenow" fragment and inserted into the pMG100 expression vector (FIG. 1) opened at the BamH1 site and also "filled in" as above. The resulting vector, pREC 2/2, expresses a modified bGH which is altered at its amino terminus as follows:

MetAspGlnPhe¹Pro²... bGH

The plasmid pREC 2/2 was digested with PstI and the fragment containing the $P_L$ promoter and the 5' end of the bGH gene (designated fragment A) was isolated. This fragment was ligated to a Pst1 fragment from pAL 500 (designated fragment B). The then resulting vector, pRec 2/3, expresses a modified bGH which is altered at its amino terminus as follows:

MetAspGlnPhe¹Pro²... bGH

Figure 2:
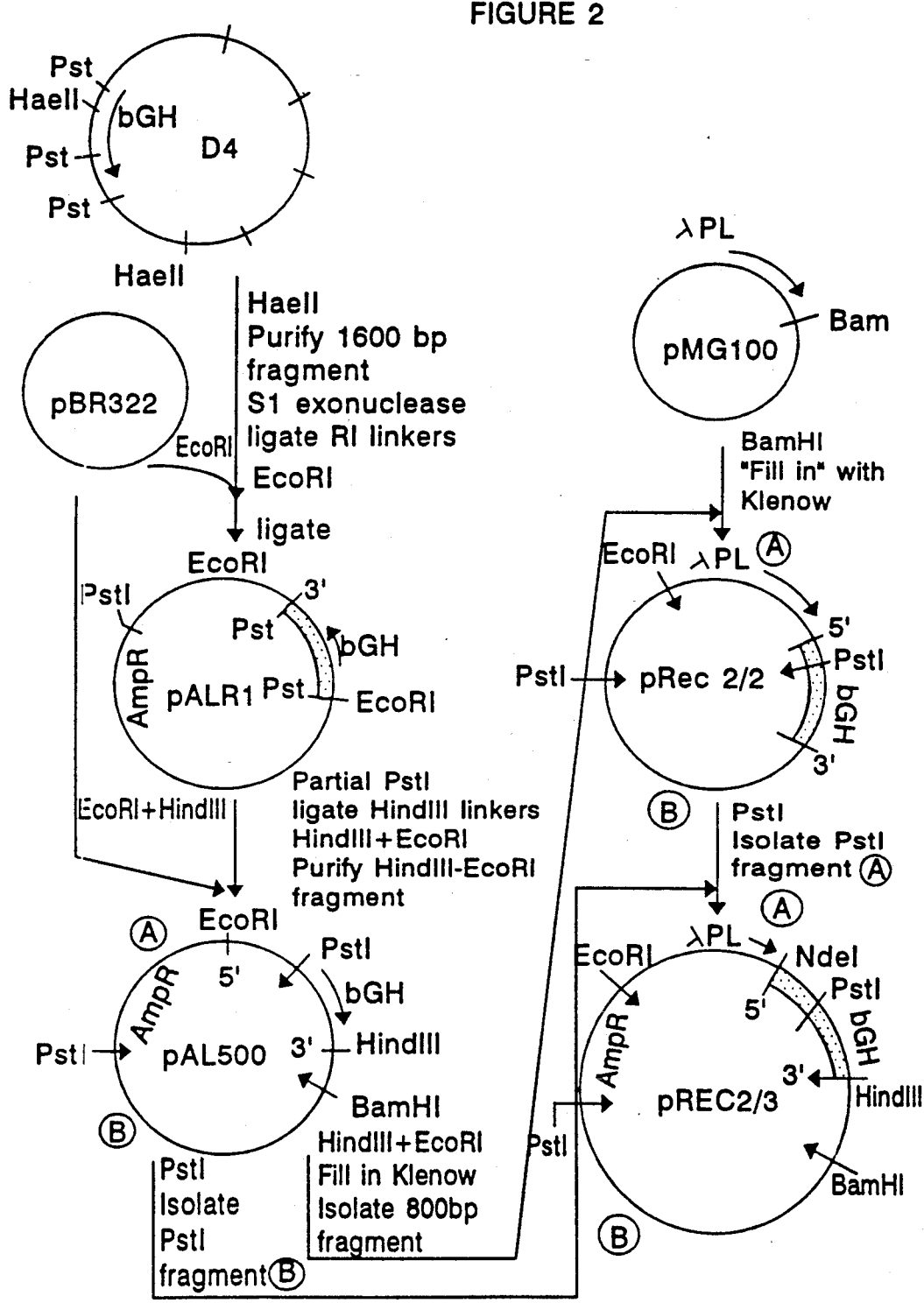
FIG. 2. Construction of pRec 2/3 plasmid. A bGH cDNA containing plasmid, $D_4$, was digested with HaeII. A resulting 1600 bp large fragment was purified and subjected to digestion at 37° C. for 5 minutes with 5 units of S1 exonuclease. A synthetic EcoR1 linker with the sequence.
Figure 3:
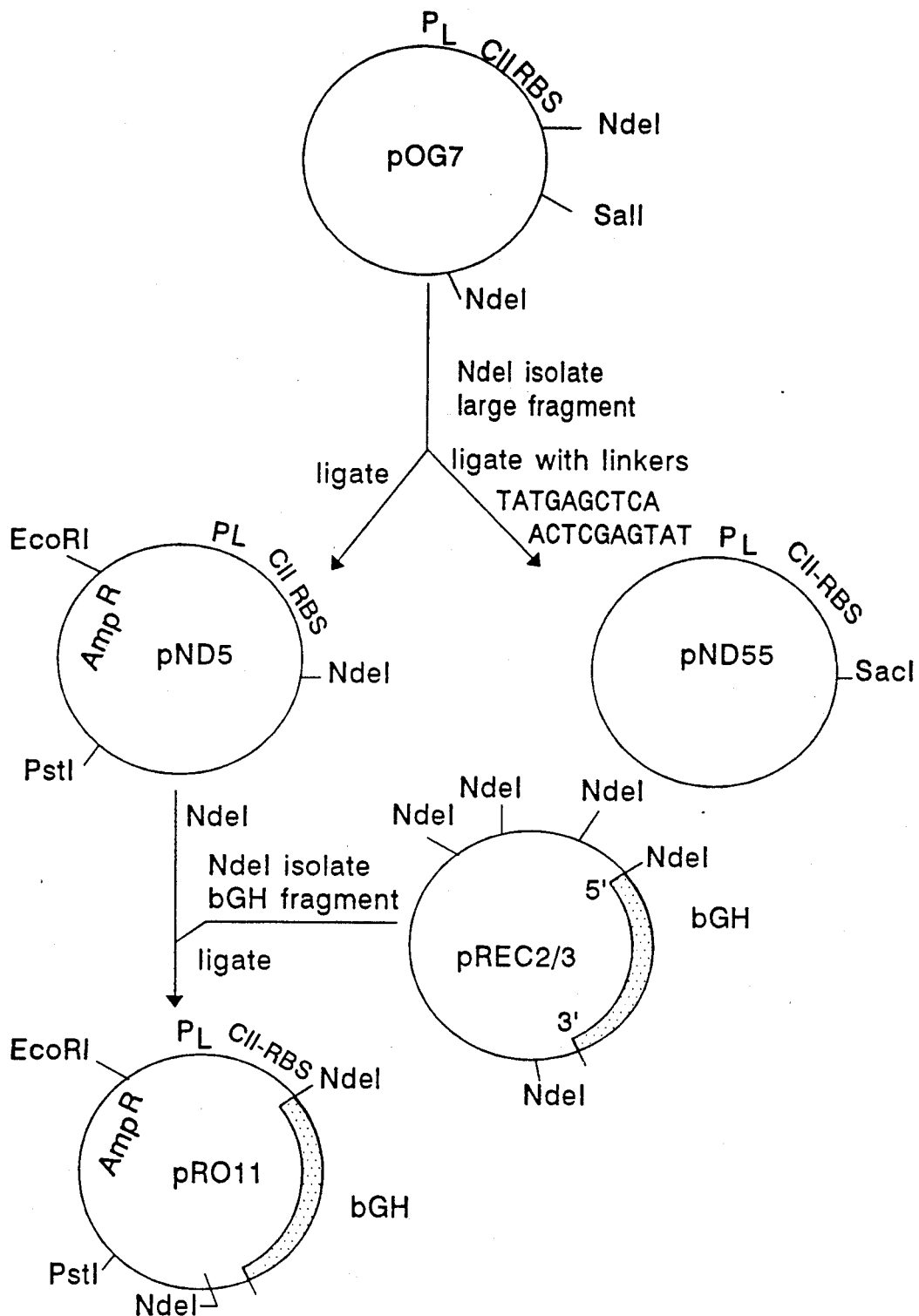

FIG. 3. Construction of expression vectors pND5, pND55 and pRO11. A plasmid pOG7 (A. Oppenheim, S. Gottesman and M. Gottesman, J. Mol. Biol. (1982) 158, 327) was cleaved with NdeI. The ends of the large fragment carrying the PL promoter $nut_L$, $t_R$ and $C_{II}$-RBS were ligated to give the pND5 expression vector. This pND5 vector DNA is opened with NdeI. Insertion of that NdeI fragment from pRec 2/3 (FIG. 2) which contains bGH cDNA results in a plasmid pRO11 appears to be a better expressor of the modified bGH described in FIG. 2 than pRec 2/3. Insertion of synthetic linkers with the sequence:

```
TATGAGCTCA
ACTCGAGTAT
``` into pOG7 cleaved with NdeI results in an expression vector pND55 which contains a unique SacI restriction site in front of ATG. When pND55 is cleaved with SacI and treated with DNA polymerase "Klenow" fragment an ATG initiation codon results which follows the PL promoter and $C_{II}$-RBS. This vector is suitable for expression of a wide variety of eukaryotic genes lacking an ATG initiation codon.

Figure 4:
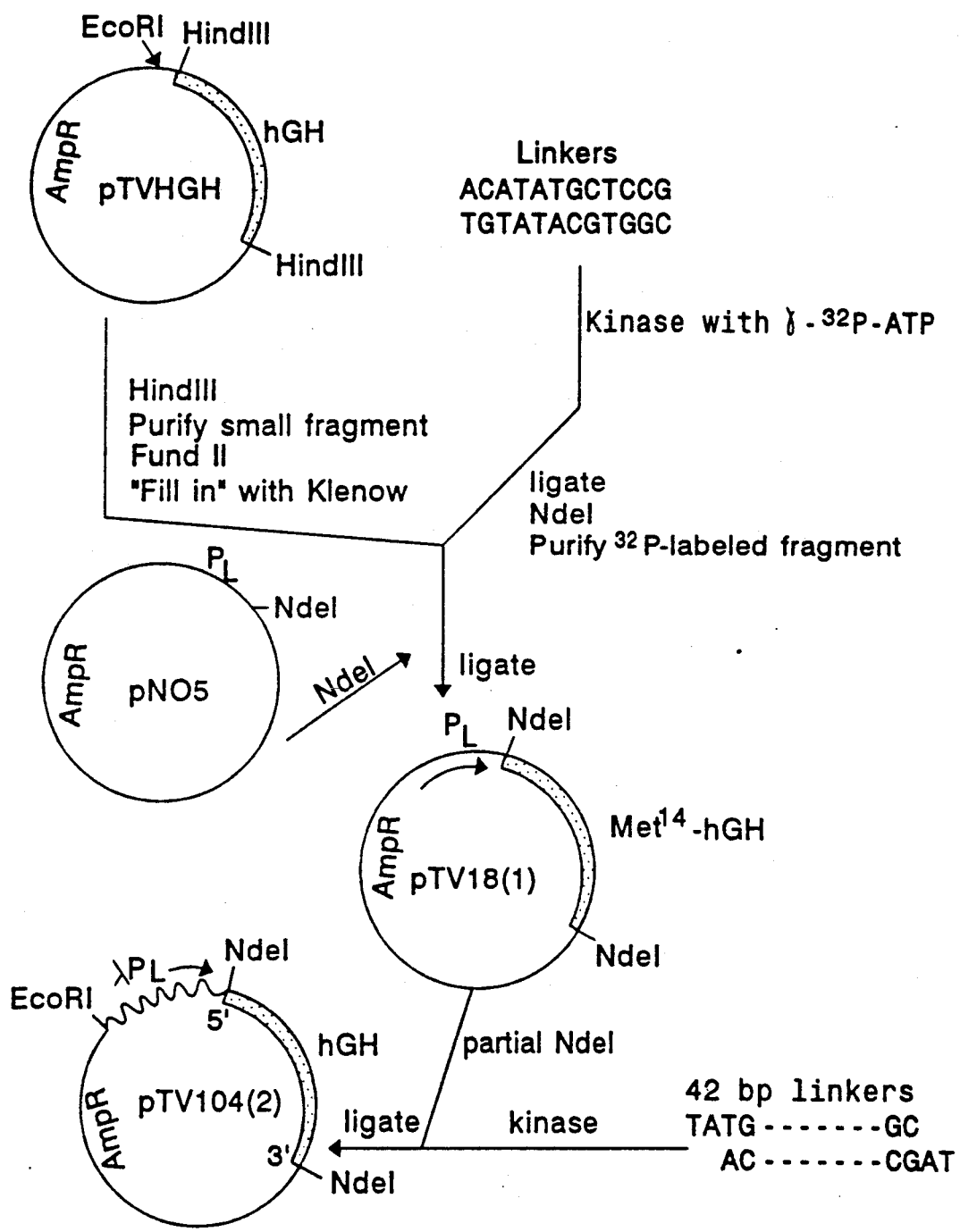

FIG. 4 Construction of pTV 18(1) and pTV 104(2). A plasmid, pTVHGH was prepared by cloning cDNA encoding hGH into the HindIII site of pBR 322 using standard methods. Meth. Enzymol. (1979) 68, 75. This plasmid was digested with HindIII. The resulting 800 base pair fragment was purified and further digested with FnuDII and "filled in" with DNA polymerase "Klenow" fragment. This treatment removes codons for the first 16 amino acids of hGH. The resulting DNA fragment is ligated with a synthetic linker which restores the codons for the sequence of hGH from Met¹⁴ and regenerates an NdeI restriction site in front of the ATG codon for Met¹⁴. After treatment with NdeI this semisynthetic DNA was inserted into the pND5 vector opened with NdeI. The resulting plasmid pTV 18(1) expresses hGH under control of the $P_L$ promoter. This hGH is an analog missing the first 13 amino acid residues and having at its N-terminus Met¹⁴.

Plasmid pTV 18(1) was partially digested with NdeI and ligated with a synthetic linker which contains the codons for amino acids 1-13 of hGH:

```
TATGTTCCCAACCATTCCATTATCCCGTCTGTTCGACAACGC
    ACAAGGGTTGGTAAGGTAATAGGGCAGACAAGCTGTTGCGAT.
```

The linker is also complementary to the NdeI site on pTV 18(1) and positions the complete hGH gene in phase with the ATG initiation codon of the pND5 expression vector (FIG. 3). Thus, the resulting plasmid, pTV 104(2), expresses native hGH with an extra methionine at the N-terminus.

Figure 5:
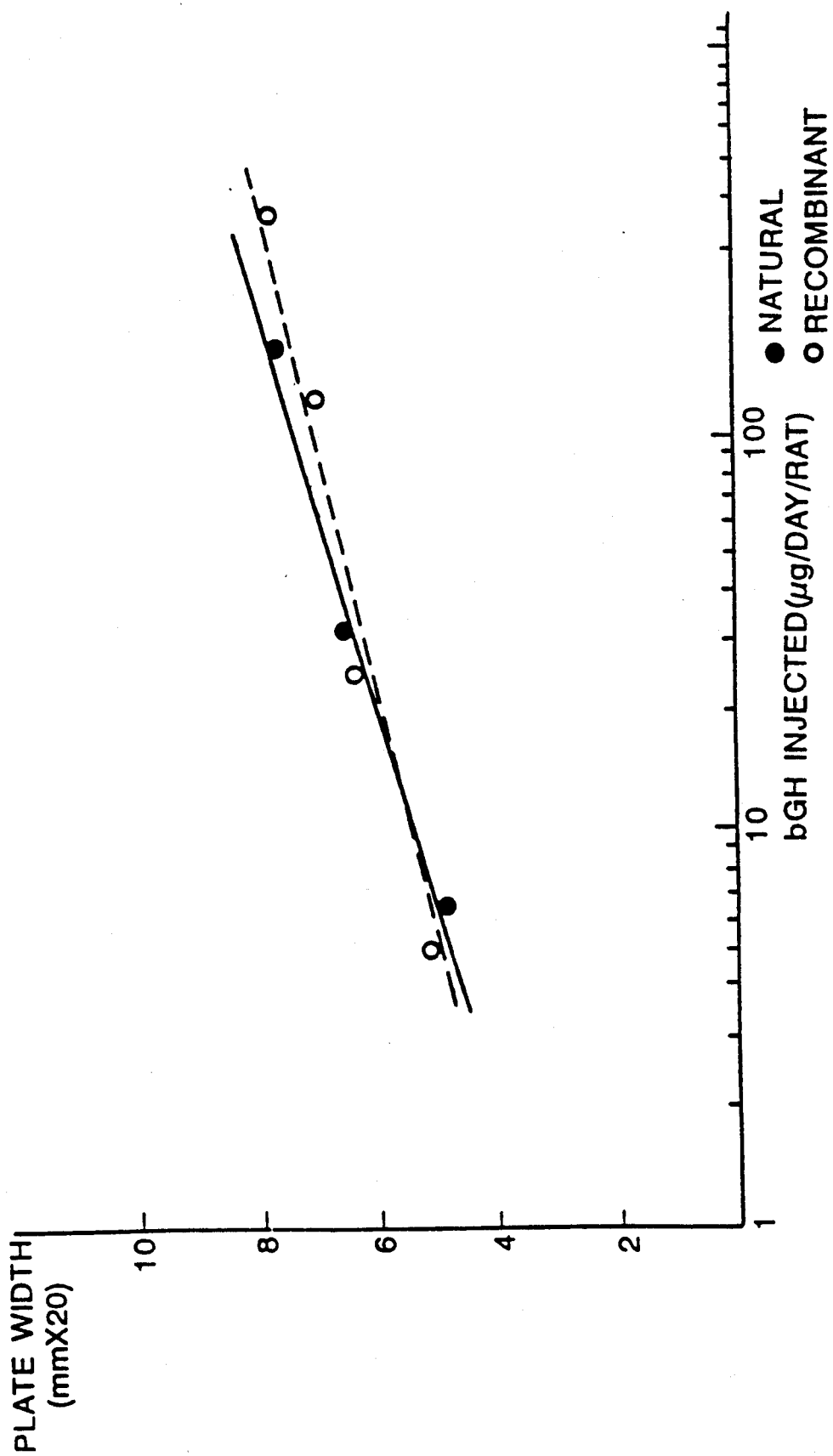

FIG. 5. Tibia test This figure shows the comparison between effect of pRec 2/3 bGH analog and authentic bGH on the bone plate growth of hypophysectomized rats.

Figure 6:
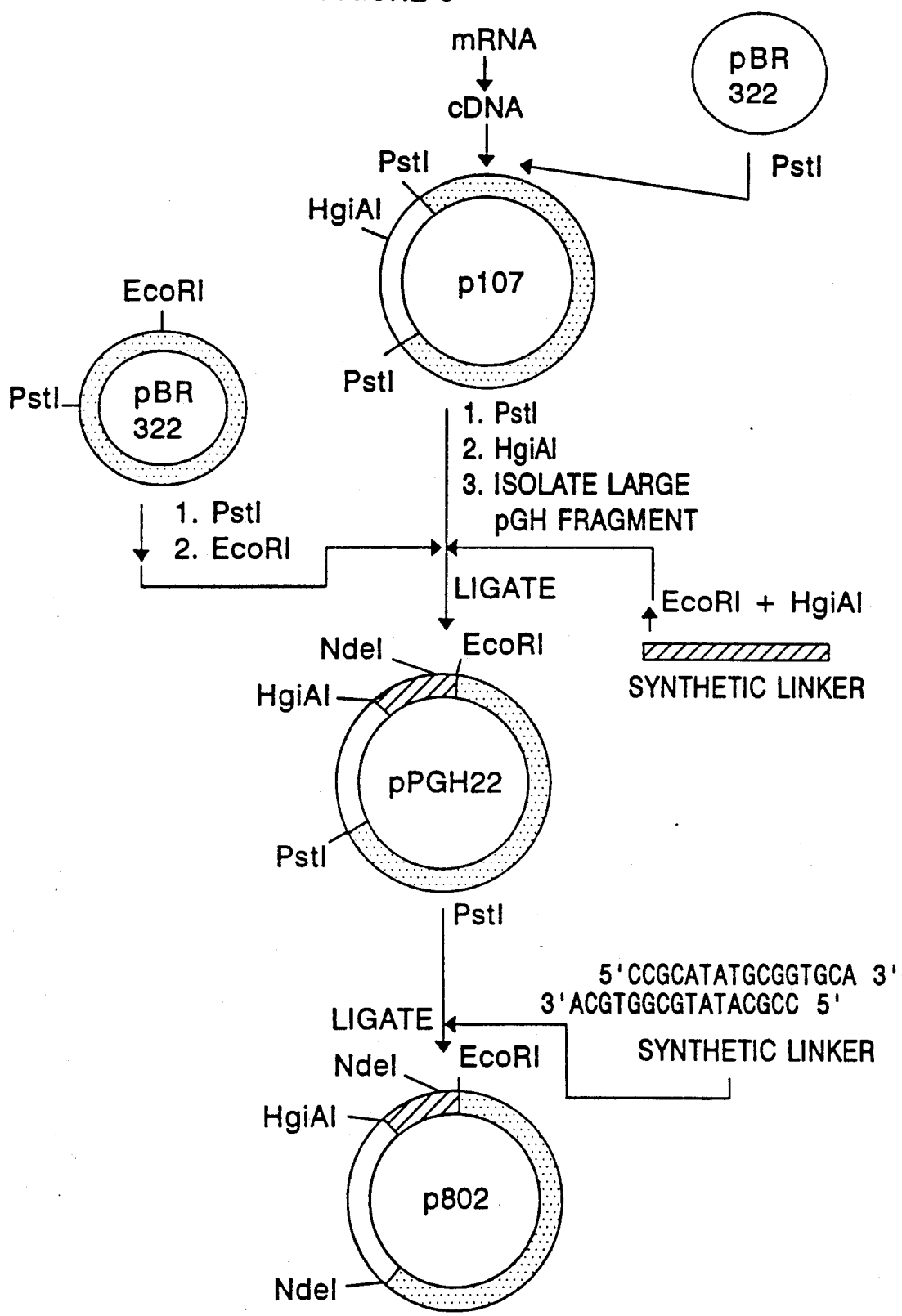

FIG. 6. Construction of p802 The construction of plasmid p802 is diagrammed in FIG. 6. p802 is a cDNA clone, containing the entire coding sequence for mature porcine growth hormone (pGH). Adjacent to the initiation codon is an NdeI restriction site. The 3' terminus of the gene is also bound by an NdeI restriction site.

Plasmid p107 was constructed by inserting pGH cDNA into pBR322 cleaved by PstI. p107 contains a complete pGH coding sequence and the leader sequence.

The mature pGH coding sequence was obtained by digesting the DNA sequence with the restrictio endonuclease Hgi AI and adding a synthetic DNA linker extending from the Hgi AI restriction site within the pGH gene to past the ATG initiation codon. The synthetic linker was designed to contain an NdeI restriction site at the ATG initiation codon for an Eco RI site upstream of the NdeI site. The sequence of the synthetic linker was:

```
5'TGAATTCATATGTTCCCAGCTATGCCTCTATCTAGTCTATTCGCTAACGCTGT
3'ACTTAAGTATACAAGGGTCGATACGGAGATAGATCAGATAAGCGATTGCGACA

GCTCAAGCTTA 3'
CGAGTTCGAAT 5'
```

Plasmid p802 was formed from pGH 22 by converting the PstI site at 3' end of the pGH cDNA to an NdeI site using synthetic DNA linkers.

Figure 7:
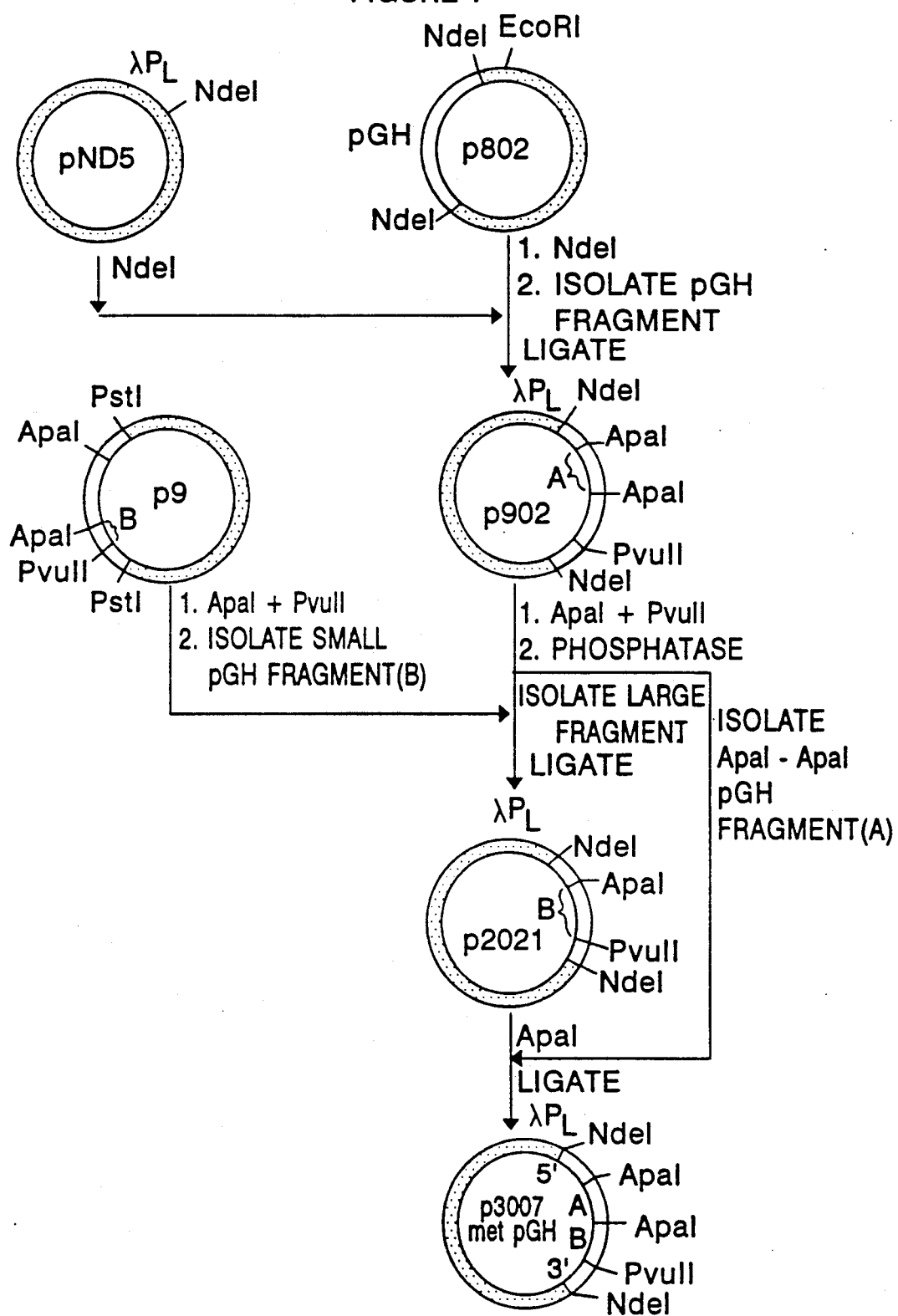

FIG. 7. Construction of p3007 Plasmid p3007 directs the expression of Met-pGH under the control of the PL promoter and cII ribosomal binding site. The expression plasmid p902 was constructed by inserting the pGH cDNA from p802 into the expression vector pND5. However, p902 directed the expression of a pGH variant which was smaller than authentic pGH by 2-3 kilodaltons. This was apparently due to a nonsense codon in the cDNA sequence.

Figure 8:
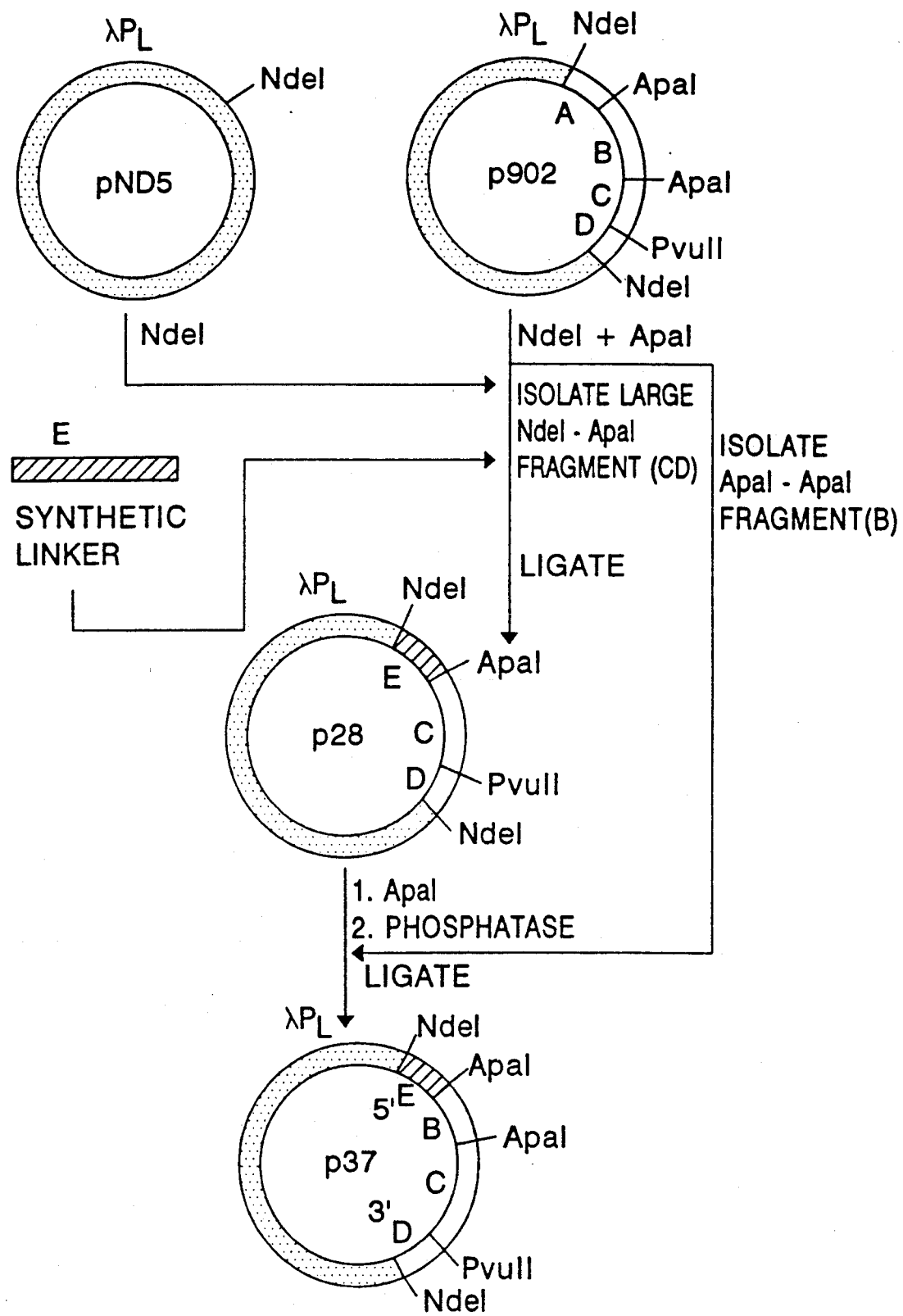

To construct a plasmid expressing full size pGH, the 3' end of the cDNA gene in p902 was replaced with 3' cDNA from plasmid p9. (Plasmid p9 was constructed in the same fashion as p107 which is diagrammed in FIG. 6.) The expression plasmid p3007 was constructed in two steps from p902 as shown in FIG. 7. p3007 directs the expression of full size met-pGH. FIG. 8. Construction of p37 Plasmid p37 was designed to express a pGH analog whose first amino acid is the methionine residue which is the fourth amino acid of mature pGH (Met$^4$ pGH). p37 was constructed from p902 (FIG. 7) by removing the 5' end of the gene and replacing it with a synthetic linker of the sequence:

```
5'TATGCCCTTGTCCAGCCTATTTGCCAACGCCGTGCTCCGGGCC 3'
3'ACGGGAACAGGTCGGATAAACGGTTGCGGCACGAGGC 5'
```

The resulting plasmid p37 directed expression of a pGH analog which was smaller than the expected size of the Met$^4$-pGH analog. This was apparently due to a nonsense codon towards the 3' end of the gene.

Figure 9:
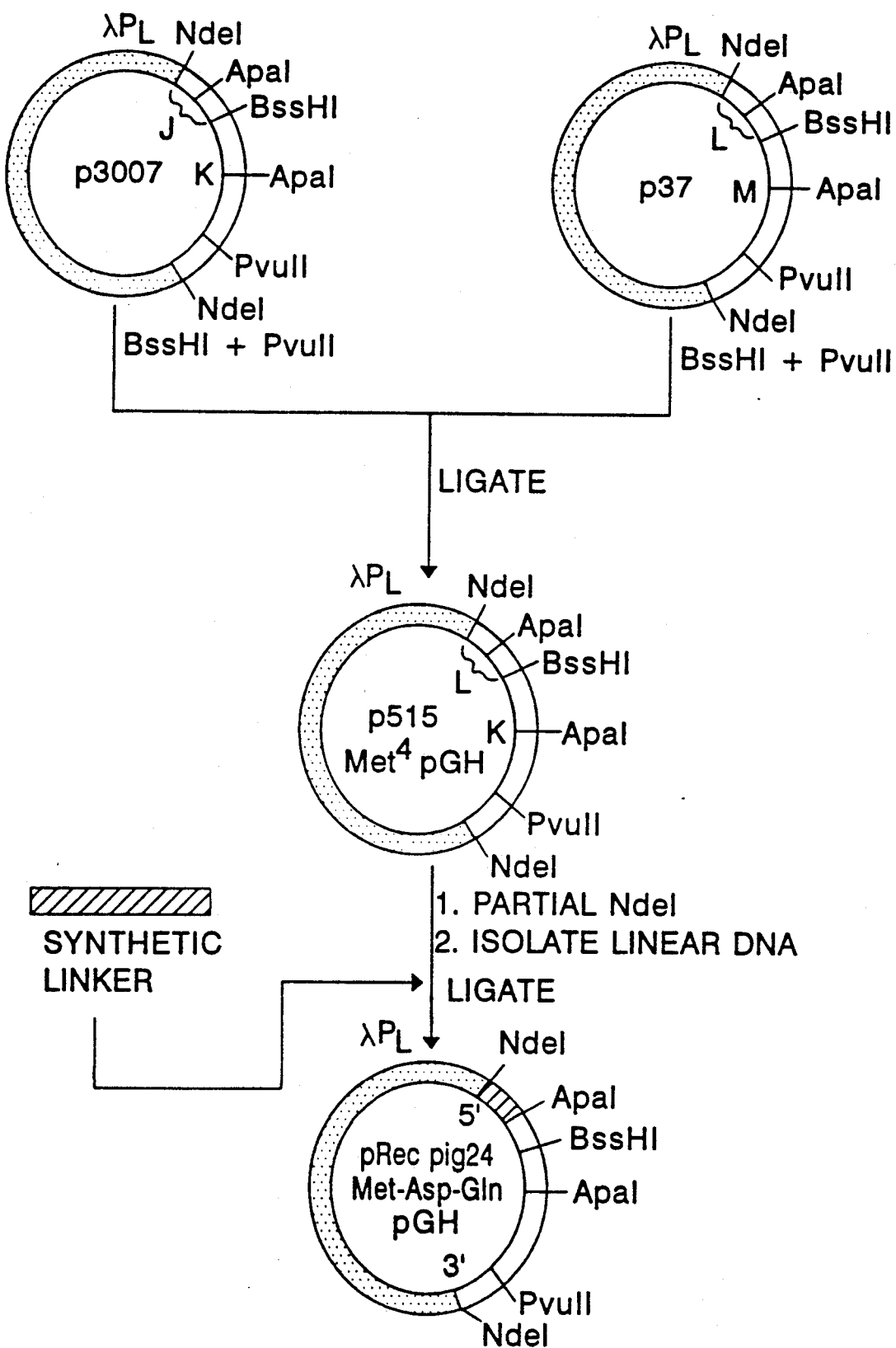

FIG. 9. Construction of pRec pig 24 pRec pig 24 directs the expression of a pGH analog of the sequence Met-Asp-Gln-pGH. pRec pig 24 was constructed from p515 which directs the expression of Met$^4$-pGH.

Plasmid p37 (FIG. 8) directs the expression of a pGH which initiates at Met$^4$ but apparently terminates early due to a nonsense codon. The 3' end of the gene in p37 was replaced with the 3' end of the gene from plasmid p3007 (FIG. 9). The resulting plasmid p515 directs the expression of the Met$^4$-pGH analog.

pRec pig 24 was constructed by introducing a synthetic DNA linker with the sequence:

```
5'TATGGATCAATTCCCAGC 3'
3'ACCTAGTTAAGGGTCGAT 5'
``` pRec pig 24 in *E. coli* A4255 has been deposited with the American Type Culture Collection under Accession No. ATCC 53433.

Figure 10:
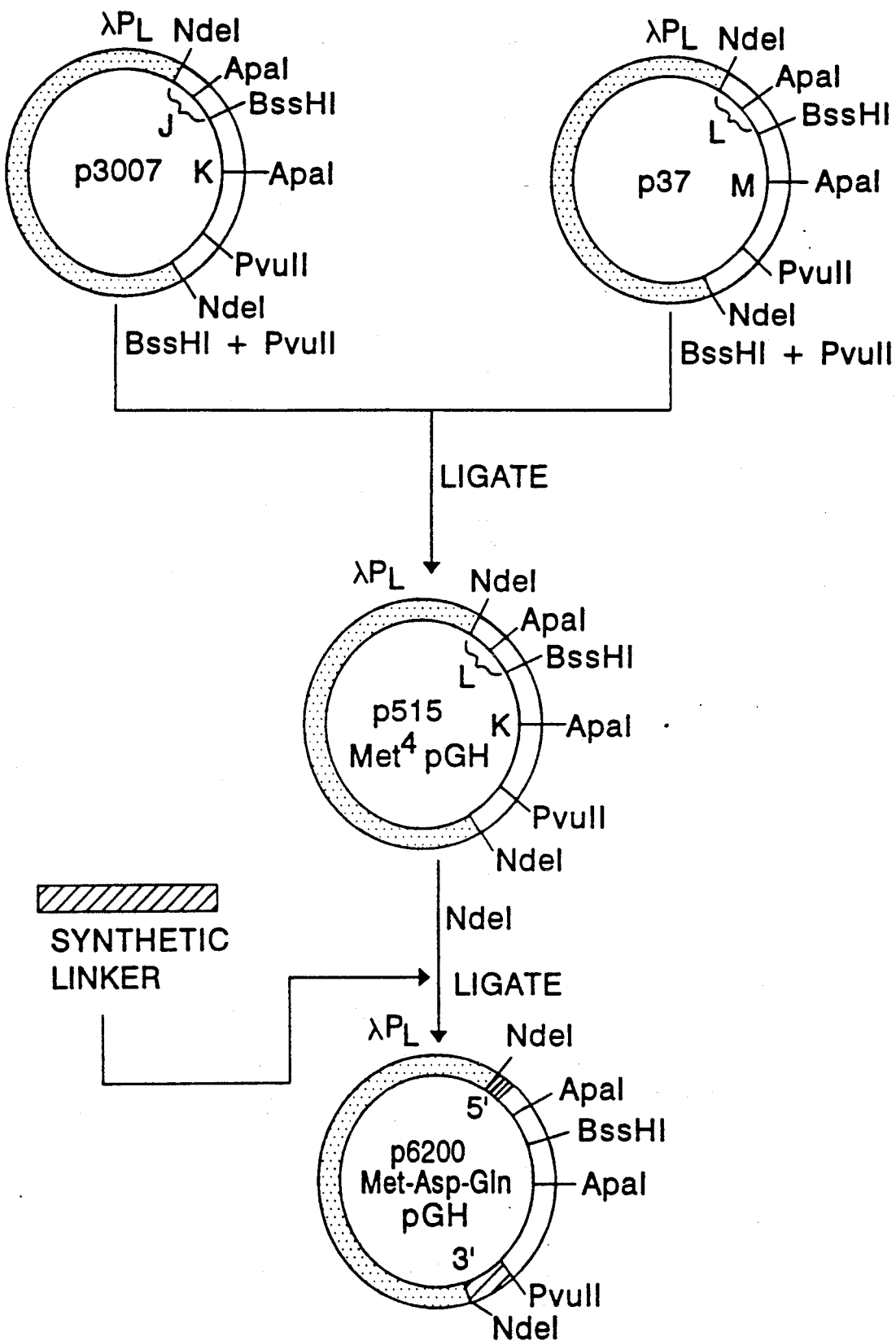

FIG. 10. Construction of p6200 The construction of p6200 parallels the construction of pRec pig 24 to the preparation of p515. To construct p6200, p515 after being digested with NdeI was ligated to the synthetic linker. The resulting plasmid, p6200, contains the synthetic linker at both the 5' and 3' ends of the pGH cDNA. p6200 directs expression of Met-Asp-Gln pGH.

Figure 11:
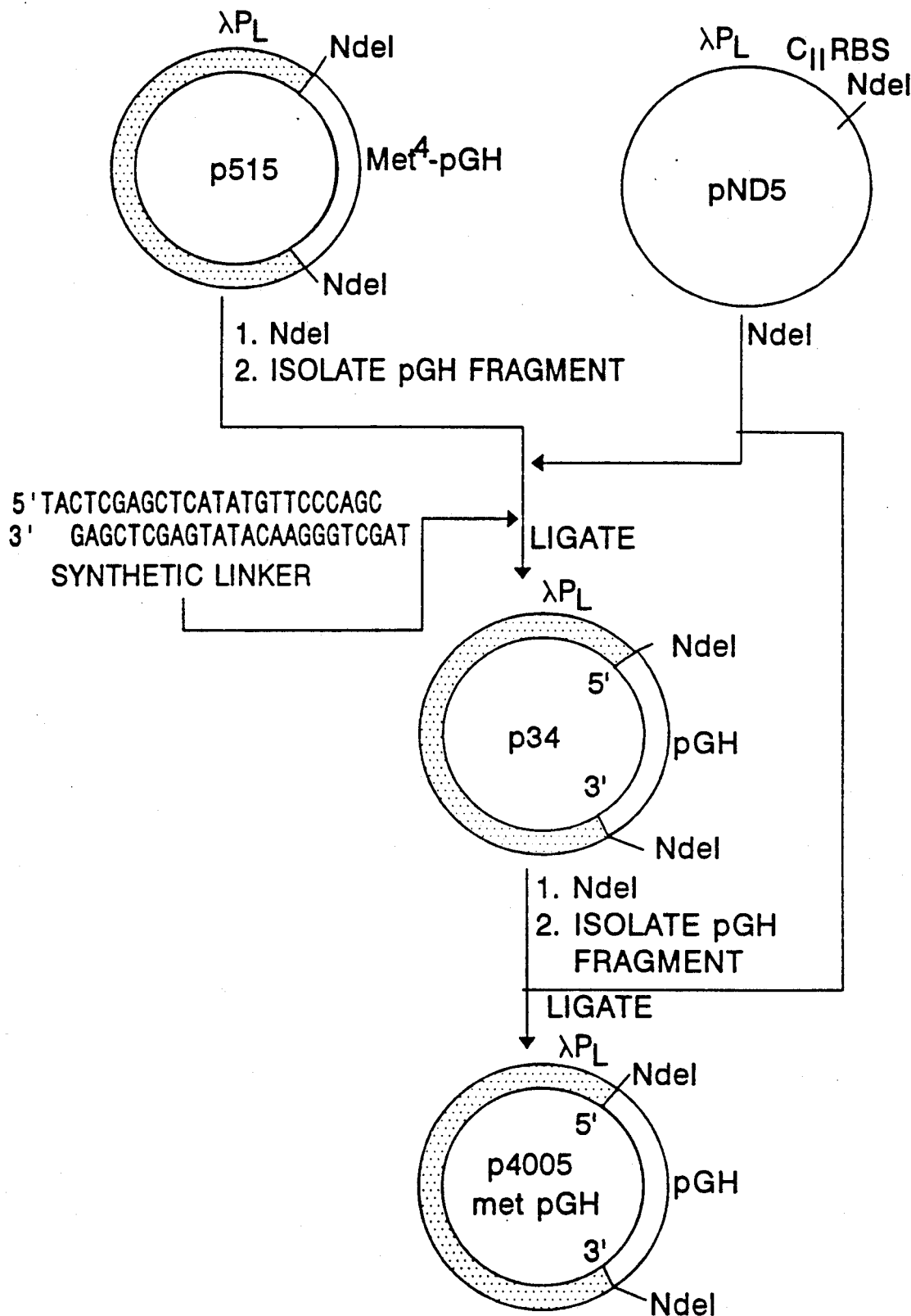

FIG. 11. Construction of p4005 p4005 was constructed from p34 which was constructed from plasmid p515.

Plasmid p515, which directs the expression of Met$^4$-pGH was cleaved with NdeI. The NdeI fragment containing the pGH cDNA was isolated and ligated to a synthetic linker, and to pND5 cleaved with NdeI. The resulting plasmid, p34, contains cDNA encoding met-pGH. However in p34, the ATG initiation codon is not located at the proper distance from the ribosomal binding site.

p34 was cleaved with NdeI, the pGH cDNA fragment was isolated and ligated to pND5 cleaved with NdeI. The resulting plasmid p4005, containing DNA identical in sequence to pGH cDNA, directs the expression of Met-pGH.

Figure 12:
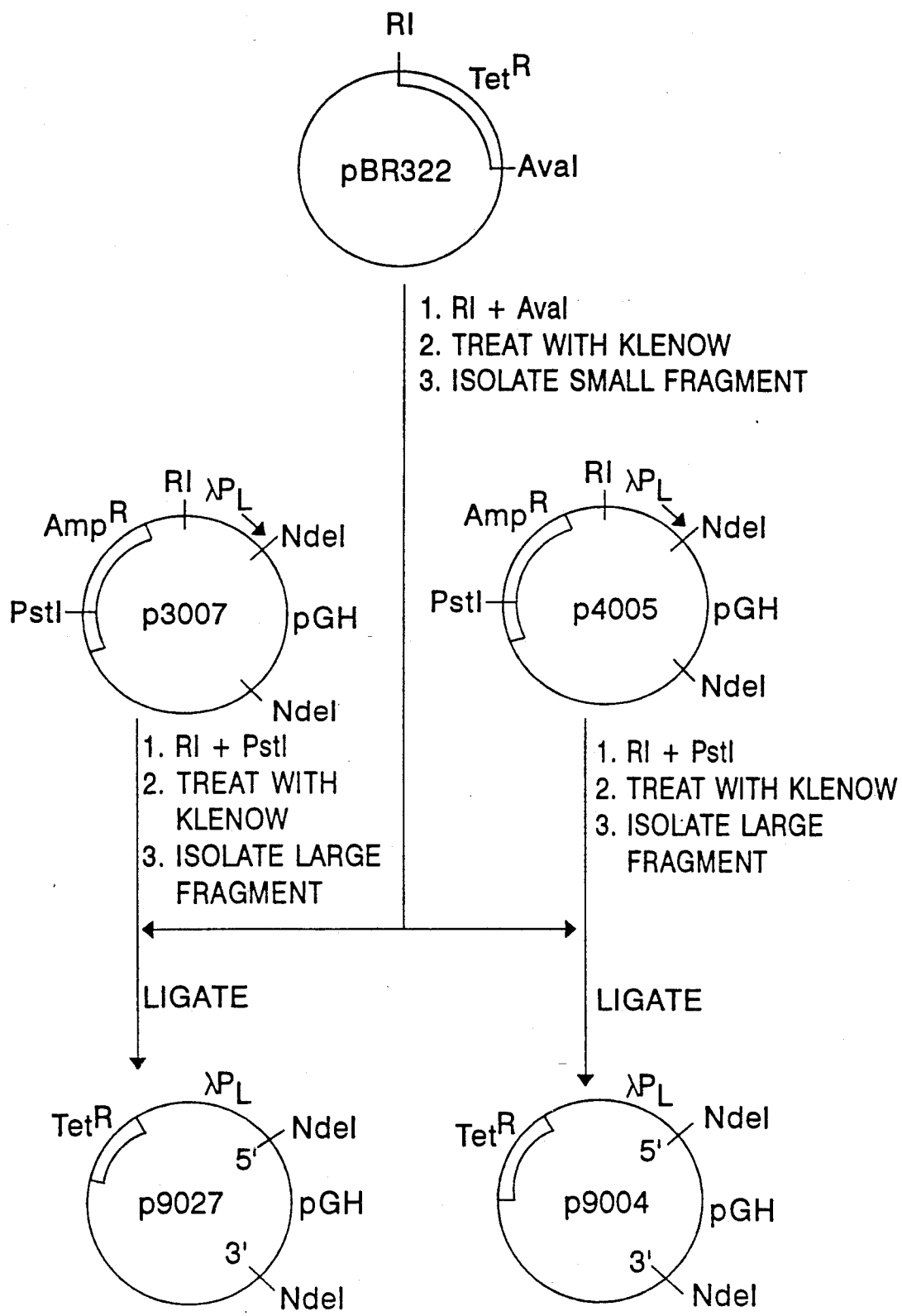

FIG. 12. Construction of Plasmids p9027 and p9004 Plasmids p9027 and p9004 (FIG. 12) were constructed from plasmids p3007 and p4005 respectively by replacing the ampicillin resistance gene with the tetracycline resistance gene from pBR322. This plasmid is advantageous in that ampicillin is not needed during fermentation. Use of ampicillin in the production of pharmaceutical products is not desirable, due to possible adverse patient reactions to traces of the ampicillin which may be found in the final product.

DETAILED DESCRIPTION OF THE INVENTION

A plasmid has been developed which enables the achievement of enhanced levels of gene expression and polypeptide expression. The plasmid is a double-stranded DNA molecule. Upon introduction into a suitable bacterial host cell containing the thermolabile repressor $C_I$ and increasing the temperature of the host to a temperature at which the repressor is destroyed, the plasmid renders the host cell capable of effecting expression of a desired gene inserted into the plasmid and production of the polypeptide encoded by the gene.

The plasmid includes in 5' to 3' order the following:

a DNA sequence which contains the promoter and operator $P_LO_L$ from lambda bacteriophage;

the N utilization site for binding antiterminator N protein produced by the host cell;

a DNA sequence which contains a ribosomal binding site for rendering the mRNA of the desired gene capable of binding to ribosomes within the host cell;

an ATG initiation codon or a DNA sequence which is converted into an ATG initiation codon upon insertion of the desired gene into the vector;

a restriction enzyme site for inserting the desired gene into the vector in phase with the ATG initiation codon; and a gene encoding the desired peptide.

The plasmid also includes a DNA sequence which contains an origin of replication from a bacterial plasmid capable of autonomous replication in the host cell and a DNA sequence which contains a gene associated with a selectable or identifiable phenotypic trait which is manifested when the plasmid is present in the host cell.

The host for use with the plasmid is Escherichia coli. The presently preferred strains are A1637, A1645, A2602 and A1563 and A2097. A1645 and A2097 are presently the more preferred strains.

A1637 was obtained from c600 by inserting transposon containing tetracycline resistance gene within the galactose operon as well as the lambda system for expression which is close to galactose operon. c600 is available from the American Type Culture Collection, as ATCC Accession No. 23724.

A1645 was obtained from A1637 by selection for Gal+ (ability to ferment galactose) as well as loss of tetracycline resistance. It still contains the lambda expression system but part of the transposon has been removed by selection. Its phenotype is C600 r−m+ gal+ thr− leu− lacZ− (λcI857 ΔH1 ΔBam N+).

Both A1637 and A1645 have been deposited with the American Type Culture Collection in Rockville, Md., U.S.A. containing various plasmids. All such deposits were made pursuant to the Budapest Treaty on the International Recognition of the Deposit of Microorganisms.

A2097 is derived from A1645. Its phenotype is A1645 lacΔχA21 proC::Tn10.

A2602 and A1563 are derived from SA500. Their phenotypes are SA500 his−ilu− gal+ Δ8(λcI857 ΔH1 ΔBam N−− and SA500 his−ilu−gal+ 8 lacZyA21 (λCI857 int2 xis1 nutL3 ΔH1), respectively. SA is available from the American Type Culture Collection as ATCC Accession No. 15746.

Prototrophic strains of Escherichia coli which enable high level pGH expression even when grown in a minimal media may also be used as hosts for the plasmids of this invention. A preferred prototrophic strain is A4255. Strain A4255 containing the plasmid pRec pig 24 has been deposited with the ATCC under Accession No. 53433.

Preferably the plasmid is a covalently closed circular double-stranded molecule. However, it is not essential that the plasmid be covalently closed.

The plasmid achieves its enhanced expression levels after the host cell is heated to a temperature at which the $C_I$ repressor is destroyed. A temperature above about 42° C. is effective for this purpose and since it is desired that unnecessary heat damage to the host cells be avoided to as great an extent as possible, it is generally desirable that the temperature never exceed 42° C. by more than a few degrees.

One important component of the plasmid is the ribosomal binding site. Suitable sites are $C_{II}$ from lambda fac-teriophage containing within it the sequence:

TAAGGAAATACTTACAT

ATTCCTTTATGAATGTA;

an oligonucleotide having the sequence:

TAAGGAAGTACTTACAT

ATTCCTTCATGAATGTA; and the major head protein gene of bacteriophage lambda having the sequence

TTTTTTTACGGGATTTTTTTATG

AAAAAAATGCCCTAAAAAAATAC.

Another component of the plasmid is the restriction enzyme site for insertion of desired genes into the plasmid in phase with the ATG initiation codon. Numerous such sites may be used. The presently preferred sites are BamH1, Sac1 and Nde1. The most preferred site is Nde1.

The plasmid also includes an origin of replication from a bacterial plasmid capable of autonomous replication in the host cell. Suitable such origins of replication may be obtained from a number of sources. Presently preferred are origins of replication derived from pBR322.

A DNA sequence which contains a gene associated with a selectable or identifiable phenotypic trait which is manifested when the plasmid is present in the host cell is also a component of the plasmid. Suitable genes include those associated with temperature sensitivity or drug resistance, e.g., resistance to ampicillin, chloramphenicol or tetracycline.

Relative to plasmids previously described in the scientific literature, the plasmids of this invention may be used to obtain enhanced expression of a wide variety of genes encoding desirable polypeptide products. Suitable genes include those encoding growth hormones, e.g., bovine, porcine, chicken or human growth hormones; superoxide dismutase; apoprotein E; viral protein 1 of foot and mouth disease virus, protein A from S. aureus, interleukin III, enzymes, or analogs of any of the preceding. By analog is meant a polypeptide having the same activity as the naturally occurring polypeptide but having one or more different amino acids at the N-terminus of the polypeptide.

The plasmid may be formed by methods well known to those skilled in the art to which the invention relates. Such methods are described in greater detail in various publications identified herein, the contents of which are hereby incorporated by reference into the present disclosure in order to provide complete information concerning the state of the art.

Figure 1:
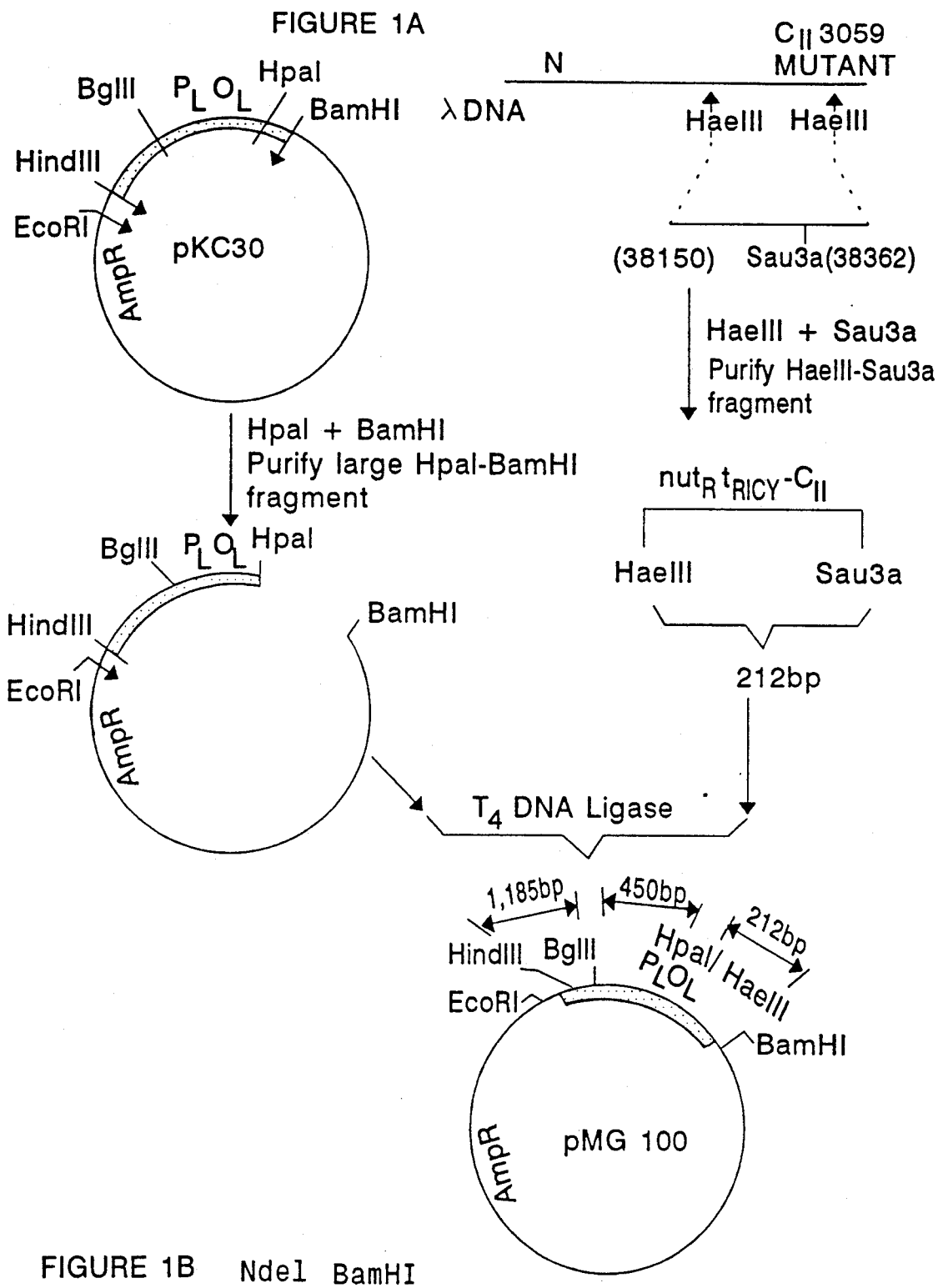
FIGS 1A and 1B. Construction of pMG100 expression vector.

One presently preferred vector is pMG100 having the restriction map shown in FIG. 1. This vector has had cDNA encoding bovine growth hormone inserted into its BamH1 restriction site. The resulting plasmid is designated pRec 2/3 bGH. Its restriction map is shown in FIG. 2. The plasmid pRec 2/3 bGH was introduced into Escherichia coli strain A1637 using conventional transformation methods. The resulting host vector system has been deposited under ATCC Accession No. 39385.

A second presently preferred vector is pND5 having the restriction map shown in FIG. 3. Bovine growth hormone cDNA has been inserted into its NdeI restriction site. The resulting plasmid is designated pRO11. Its restriction map is also shown in FIG. 3. The plasmid pRO11 was introduced into *E. coli* strain A1637 via transformation. The host vector system which resulted has been deposited under ATCC Accession No. 39390.

The vector pND5 has also been used to clone human growth hormone. One plasmid designated pTV 18(1) and another designated pTV 104(2) have been created by inserting hGH cDNA into the NdeI restriction sites. pTV 18(1) is shown in FIG. 4. It has been introduced into *E. coli* strain A1637 via transformation. The resulting host vector system has been deposited under ATCC No. 39386. pTV 104(2) is shown in FIG. 4. It also has been introduced into *E. coli* strain A1637. The resulting host vector system has been deposited under ATCC Accession No. 39384.

The vector pND5 has also been used to clone porcine growth hormone. Plasmids expressing various analogs of pGH have been created by inserting pGH cDNA into the NdeI restriction sites of the vector. Such plasmids include: pRec pig 24 shown in FIG. 9 and p6200 shown in FIG. 10, both of which direct expression of the met-asp-gln-pGH analog; p3007 shown in FIG. 7 and 4005 shown in FIG. 11 which direct the expression of the met pGH analog: and p515 shown in FIGS. 9 through 11 which directs expression of Met$^4$ pGH. The plasmid pRec pig 24 has been introduced into *E. coli* strains A4255 and A2097 via transformation. The plasmid pRec pig 24 in A4255 has been deposited with the American Type Culture Collection under ATCC Accession No. 53433. The plasmid p3007 has been introduced into *E. coli* A1645 via transformation.

Using the same approach other plasmids may be prepared by inserting into the restriction enzyme site of a vector of the invention a gene encoding a desired polypeptide.

The preceding specific host vector systems involve *E. coli* A1637 and A1645. However, as previously indicated other strains have been used including A2602 and A2097. These host vector systems may be used to produce polypeptides such as bovine, porcine and human growth hormones. To do so, the host vector system is grown under suitable conditions permitting production of the polypeptide which is then recovered.

Suitable conditions involve growth of the host vector system for an appropriate period of time at about 30° C. until the desired optical density is reached, followed by continued growth at about 42° C. for an additional period of time, if the growth is carried out on a suitable minimal medium. Desirably, the additional period of time is about 2 hours.

Suitable conditions also include growth of the host-vector system for an appropriate period of time at about 30° C. until the desired optical density is reached followed by continued growth at 42° C. for about 15 minutes, followed by further growth at 38° C. for about 2 hours when the growth is carried out on a suitable rich medium, e.g., casein hydrolysate.

By means of the preceding method a number of bGH, hGH and pGH analogs have been prepared. These have the activity of the naturally occurring hormones.

bGH analogs have the activity of natural bGH and an identical amino acid sequence except for variations at the Nterminus of up to five (5) amino acids. Examples include the following:

1) amino acid methionine added to N-terminus of the phenylalanine form of bGH.

2) amino acid methionine added to N-terminus of the alanine form of bGH.

3) amino acid sequence Met-Asp-Pro added to N-terminus of the phenylalanine form of bGH.

4) amino acids up to methionine (4 position) removed from N-terminus of phenylalanine form of bGH.

hGH analogs have the activity of natural hGH and an identical amino acid sequence except for variations at the Nterminus. An example is the following:

1) amino acid methionine added to N-terminus of natural hGH.

pGH analogs having the activity of naturally occurring pGH have also been prepared Examples of pGH analogs having the activity of natural pGH and a similar amino acid sequence except for variations at the N terminus include the following:

1) amino acid methionine added to the N terminus of the phenylalanine form of natural pGH;

2) amino acid sequence Met-Asp-Gln added to the N terminus of the phenylalanine form of pGH; and 3) amino acids up to methionine (4 position) removed from the N terminus of pGH.

Veterinary compositions may be prepared which contain effective amounts of one or more bGH analogs and a suitable carrier. Such carriers are well-known to those skilled in the art. The analogs may be administered directly or in the form of a composition to a bovine in order to increase milk or meat production.

Pharmaceutical compositions may be prepared which contain effective amounts of one or more hGH analogs and a suitable carrier. Such carriers are well-known to those skilled in the art. The analogs may be administered directly or in the form of a composition to a human subject, e.g., one afflicted by dwarfism, to treat deficiencies in hGH production by the subject.

Veterinary compositions may also be prepared which contain effective amounts of one or more pGH analogs and a suitable carrier. Such carriers are well-known to those skilled in the art. The pGH or analog may be administered directly or in the form of a composition to the porcine to stimulate increased milk or meat production or to improve the porcine carcass composition by reducing the backfat thickness, by increasing the weight of lean cuts (e.g., trimmed ham, loin, picnic and Boston butt) or by increasing the loin eye area.

EXAMPLES

The examples which follow are set forth to aid in understanding the invention but are not intended to, and should not be so construed as to, limit its scope in any way. The examples do not include detailed descriptions for conventional methods employed in the construction of vectors, the insertion of genes encoding polypeptides of interest into such vectors or the introduction of the resulting plasmids into bacterial hosts. Such methods are well-known to those skilled in the art and are described in numerous publications including the following:

Principles of Gene Manipulation, An Introduction to Genetic Engineering, 2nd Edition, edited by R. W. Old and S. B. Primrose, Univ. of Calif. Press (1981)

Met. Enzymol. vol. 68, Recombinant DNA, edited by Ray Wu

Met. Enzymol. vol. 65, Nucleic Acids (Part 1), edited by Lawrence Grossman and Kivie Moldave T. Maniatis, E. F. Fritsch and J. Sambrook, Molecular Cloning; A Laboratory Manual, Cold Spring Harbor Laboratory, N.Y. (1982)

H. V. Bernard et al., Gene (1979) 5, 59

A. B. Oppenheim et al., J. Mol. Biol. (1982) 158, 327

E. Remaut et al., Gene (1981) 15, 81

EXAMPLE 1

Expression Vectors

As used herein the term expression vector refers to a group of plasmids useful for expressing desired genes in bacteria, particularly in *E. coli*. The desired gene may be inserted into the expression vector or alternatively, the promoters on the expression vector may be excised and placed in front of the desired gene.

$P_L$ EXPRESSION VECTORS

A. pMG 100 pMG 100, as shown in FIG. 1 and described in detail under Description of the Figures is composed of λDNA inserted into the multicopy plasmid pBR322. The salient features of the λ DNA is that it contains the λ$P_L$ promoter, N utilization sites L and R ($nut_L$ and $nut_R$) the right ward termination site (trI), the $C_{II}$ ribosomal binding site and an ATG initiation codon. Other features are shown in FIG. 1.

pMG100 was prepared from pKC30. pKC30 in turn was prepared by subcloning of λ$P_L$ promoter in the following manner.

λ phage DNA was digested with XhoI and SmaI restriction endonucleases and the unique fragment comprised of 6393 base pairs was purified and subsequently digested with HindIII and BamH1 restriction endonucleases. The resulting fragment comprised of 2397 base pairs and containing $P_L$ promoter was purified and ligated into a pBR322 DNA large fragment isolated from the HindIII and BamH1 digest. The subclone was identified by colony hybridization, recovered and plasmid DNA isolated (Oppenheim, A. et al., J.Mol.Biol. (1982) 158, 327.)

This plasmid and its derivatives containing eukaryotic genes may be maintained in suitable *E. coli* hosts. The most important feature of the host is that it provides the thermosensitive repressor CI857 and the antitermination N protein. (Gottesman, M. E. et al., J.Mol.Biol. (1978) 140, 197).

This vector has numerous advantages over previously described expression vectors including:

1. Extremely High Levels of Expression

This vector is capable of directing expression of foreign proteins in *E. coli* at levels as high as 15–25% of the total cellular protein.

2. Thermoinducible Regulation of Expression

The $P_L$ promoter is inactive when the $C_I$ repressor is bound to it. The CI857 repressor is thermosensitive, that is, it binds to the promoter at 30° C. but is inactivated at 42° C. Thus, by increasing the temperature of fermentation to 42° C. the host bacteria are induced to produce the desired protein.

The advantages of such a system include the following:

(a) a foreign protein which is toxic to *E. coli* can be produced when desired thus avoiding cell death early in the fermentation process.

(b) overproduction of a protein may stabilize it and prevent proteolytic degradation. (Cheng, Y. E. et al., Gene (1981) 14, 121). Thus, "instantaneous" overproduction using a tightly regulated promoter such as $P_L$ may be preferable to continuous low level production.

3. High Copy Number

The $P_L$ promoter in pMG100 is found on a plasmid with a high copy number in distinction to λ itself which is present in low copy numbers in *E. coli*. This increases expression levels.

4. Ribosome Binding Site and Initiation Codon

This expression vector contains a strong procaryotic ribosomal binding site (RBS) as well as a translation initiation codon (ATG). Thus, any eukaryotic gene may be cloned without the need for adding an initiation codon. Furthermore, the efficient RBS increases levels of expression.

5. Convenient Restriction Site

The expression vector has a BamHI site located directly following the ATG initiation codon which permits proper positioning of the desired gene in order to achieve optimal expression.

6. Nut Site

N protein which is provided by the host binds to Nut site on the expression vector and thereby prevents termination of transcription at the $t_{R1}$ site.

B. pND5

As shown in FIG. 3, pND5 contains the $P_L$ promoter and the other important components of the expression vectors of this invention. It includes a unique NdeI site immediately after the ribosomal binding site. The ribosomal binding site differs from the normal $C_{II}$ site. It has the sequence:

TAAGGAAGTACTTACAT

ATTCCTTCATGAATGTA

It may be derived from a mutant or may be chemically synthesized. As described in detail under Description of the Figures pND5 was derived from pOG7. (Oppenheim, A., et al., J.Mol.Biol. (1982) 158, 327) This vector does not contain a translation initiation codon. It appears to provide superior expression of modified bGH and hGH, particularly enhanced yield relative to pMG100 containing a bGH analog.

EXAMPLE 2

Bovine Growth Hormone

The starting point for bGH cDNA modifications is plasmid D4 which has been described previously. (Keshet, E. et al, Nucleic Acids Research (1981) 9, 19). The D4 plasmid is also described in pending U.S. patent application, Ser. No. 245,943, filed Mar. 20, 1981, claiming priority of Israel patent application, Ser. No. 59,690 filed Mar. 24, 1980. It has previously been deposited with the American Type Culture Collection in an *E. coli* host under ATCC No. 31826.

I. pRec 2/3 bGH

The construction of pRec 2/3 is shown in FIG. 2 and described in the Description of the Figures. bGH cDNA from D4 has been manipulated prior to insertion into PMG100 to provide the correct reading frame.

pRec 2/3 has been introduced into various *E. coli* strains including A1637 by transformation using known methods. A1637 containing pRec 2/3 has been deposited under ATCC No. 39385. This strain produces upon growth an analog of bGH having the amino acid sequence Met-Asp-Gln added to the N-terminus of the phenylalanine form of natural bGH. The amount of bGH analog produced by pRec 2/3 was about 23% of the total protein produced by the bacteria as calculated from scanning of Coomasie stained SDS polyacrylamide gels.

II. pRO11

The construction of pRO11 is shown in FIG. 3 and described in the Description of the Figures. bGH cDNA from D4 was modified and inserted into pND5. A fragment of pRec 2/3 was- inserted into pND5 to produce pRO11.

pRO11 has been introduced into *E. coli* A1637 by transformation. The resulting host vector system has been deposited under ATCC No. 39390 This strain when grown produces the same analog as pRec 2/3. Preliminary results indicate that pRO11 produces up to 20% more bGH analog than pRec 2/3. The methods used to grow the strain, recover the bGH analog produced and purify it are the same as those described for pRec 2/3 in Example 4.

EXAMPLE 3

Human Growth Hormone

The starting point for hGH cDNA was cloning of the cDNA from mRNA purified from hypophyses tumor from acromegalic patients into the HindIII site of pBR322.

I. pTV 18(1)

The construction of PTV 18(1) is shown in FIG. 4 and described in the Description of the Figures. hGH cDNA was manipulated prior to insertion into pND5 to provide the correct reading frame.

pTV 18(1) was introduced into *E. coli* A1637 by transformation. The resulting bacteria have been deposited under ATCC No. 39386. This strain upon growth produces an analog of hGH having the sequence of natural hGH beginning with Met[14] and lacking amino acids 1-13. The amount of hGH analog produced by pTV 18(1) was about 8% of the total protein produced by the bacteria.

II. pTV 104(2)

The construction of pTV 104(2) is shown in FIG. 4 and described in the Description of the Figures. hGH cDNA was manipulated prior to insertion into pND5 to provide the correct reading frame.

pTV 104(2) was introduced into *E. coli* A1637 by transformation. The resulting bacteria have been deposited under ATCC No. 39384. This strain upon growth produces an analog of hGH having the sequence of natural hGH preceded by Met at the N-terminus. The amount of hGH analog produced by pTV 104(2) was above 25% of the total protein produced by the bacteria.

EXAMPLE 4

Growth of pRec 2/3

Stock Cultures: Stock cultures of pRec 2/3 in A1637 are grown on BHI medium (see inoculum), then diluted twofold with 87% glycerol containing phosphate citrate buffer, and stored at −70° C.

Inoculum: Inoculum is propagated in BHI medium (37 g/l brain heart infusion (DIFCO). Sterile medium in shake flask is inoculated from stock culture and incubated 15 hours on shaker at 30° C., 200 r.p.m. Subsequent stages in inoculum propagation are carried out in stirred aerated fermentors. Sterile medium is inoculated with 0.2 ml flask culture per 1, and incubated 15 hours at 30° C., pH 7±0.5 with agitation and aeration to maintain dissolved oxygen level above 20% air saturation.

Production: Production medium contains:

| Lactalbumin hydrolysate (enzymatic) | 20 g/l |
|---|---|
| Yeast extract | 10 g/l |
| K$_2$HPO$_4$ | 2.5 g/l |
| NaCl | 10 g/l |
| Ampicillin | 0.1 g/l |
| Biotin | 0.1 mg/l |
| Thiamine | 1 mg/l |
| Trace elements solution | 3 ml/l |

Ampicillin, biotin and thiamine in solution are filter sterilized separately and added to the sterile production medium before inoculation. Sterile glucose solution is added initially to supply 10 g/l, and during the induction and expression procedure to maintain glucose above 1 g/l. Trace elements solution contains:

| MgSO$_4$.7H$_2$O | 170 g/l |
|---|---|
| FeCl$_3$ | 16 g/l |
| ZnCl$_2$.4H$_2$O | 2 g/l |
| CoCl$_2$.6H$_2$O | 2 g/l |
| Na$_2$MoO$_4$.2H$_2$O | 2 g/l |
| CaCl$_2$.2H$_2$O | 1 g/l |
| CuCl$_2$ | 1 g/l |
| H$_3$BO$_3$ | 0.5 g/l |
| Conc. HCl | 100 ml/l |

The medium is inoculated with 5-10% inoculum culture and incubated at 30° C. Agitation-aeration rates are set to maintain dissolved oxygen level above 20% air saturation. The pH is maintained at 7±0.2 with NH$_3$. Once cell concentration reaches about 3 g/l (OD$_{660}$=10) induction is started.

Temperature is raised to 42° C. Maintained there for 15 minutes, then lowered to 38° C. Following incubation at 38° C. for 1-1½ hours, the culture is chilled, and cells are recovered by centrifugation for hormone purification.

Recovery of bGH

One kilogram of bacterial cells is suspended in 10 volumes of the solution containing 50 mM Tris-Cl (pH 7.4), 50 mM EDTA and 25% sucrose in a Waring blender, with a control of blender's speed to minimize foaming. The homogeneous suspension is continuously passed through a Dynomill cell disruptor (Willy A. Bachofen, Basel) and the homogeneous suspension of disrupted cells is clarified first by centrifugation in a Sharpless centrifuge followed by a continuous centrifugation at 20,000 rpm in a Sorvall centrifuge. The precipitate from both centrifugation steps is collected, washed with 50 mM Tris-Cl (pH 7.4) and resuspended in 500 ml of the same buffer. Lysozyme is added to a final concentration of 2 mg/ml and the suspension is incubated for 1 hour at 37° C. Triton X-100 is then added to a final concentration of 1%, the suspension is cooled to 4° C. and centrifuged at 20,000 rpm for 20 minutes in a Sorvall SS34 rotor. The precipitate is collected, washed twice with 50 mM Tris-Cl, resuspended in 500 ml of 50 mM Tris-Cl (pH 7.4), 5 mM MgCl2 and deoxyribonuclease is added to a final concentration of 20 µg/ml. After incubation for 30 minutes at room temperature the precipitate is collected as above, washed twice with 500 ml of 20 mM Tris-Cl (pH 7.4), 100 mM NaCl and 10 mM EDTA, followed by two washings with 500 ml of distilled water. The precipitate is collected by centrifugation and can be stored at −20° C. for an indefinite time. At this stage the bGH is 80% pure as judged by sodium dodecyl sulfate-gel electrophoresis. The yield is approximately 15 g of bGH.

Purification of bGH

One hundred g of precipitate is suspended in 40 ml distilled water and solubilized by titration with 0.5 M NaOH, pH 11.8. The solution is then sonicated for 2 minutes and clarified by centrifugation at 20,000 rpm in a Sorvall SS 34 rotor for 20 minutes. The solution is then applied onto a Sepharose CL-6B column (5×100 cm) equilibrated with 6.5 mM borate buffer, pH 11.8. Column is developed at the rate of 100 ml/hr and fractions of 12 ml are collected. The first peak off the column is discarded. The following two peaks are separated and pooled. The first represents aggregated bGH with low activity; the second bGH with high activity.

A DEAE-Sephacel (25 g/100 gr. equiv. ppt) column is equilibrated with 6.5 mM borate buffer, pH 9.0. The second bGH peak is brought to pH 9.0 with HCl loaded on the DEAE Sephacel column at a rate of 250 ml/hr. The column is washed with 7.5 ml of 6.5 mM borate buffer, pH 9.0, eluted with 6.5 mM borate buffer, pH 9.0 containing 75 mM NaCl. The fractions with $OD_{280}$ above 0.3 are pooled, dialysed against $H_2O$ in Millipore Pellicon dialysis apparatus and then lyophilized.

EXAMPLE 5

Activity of bGH Analog Produced by pRec 2/3

1. Radioimmunoassay comparison of bGH analog with natural bGH

A solution containing 100 ng/ml bGH analog was prepared in phosphate buffered saline (1% BSA). This solution was diluted serially to concentrations of 50, 25, 12.5, 6.25, 3.12, 1.56 and 0.78 µg/l. Duplicate 0.1 ml aliquots of these solutions were submitted to RIA using a double antibody procedure. The dilution curve was comparable to that obtained with natural bGH.

2. Radioreceptor binding Assay

A radioreceptor binding assay was performed with rabbit liver membranes as described by T. Tushima and H.G. Freisen (Y. Chin., Endocr. Metab. (1973) 37, 334 using $^{125}$I-hGH as the tracer and authentic bGH solutions for the construction of calibration curves. Samples were incubated in triplicate for two hours at room temperature in 0.3 ml of assay buffer (50 mM Tris, 15 mM $CaCl_2$ and 5 mg/ml bovine serum albumin, pH 7.6). The tubes contained $^{125}$IhGH (20,000 cpm of preparation of 30-60 µci/µg), 150-250 µg liver membrane protein and either natural bGH (1-100 µg) or extracts of bacterial bGH. The result demonstrated that the bGH activity of the bGH analog is comparable to that of natural bGH.

3. Tibia Test

The bioactivity of the pRec 2/3 bGH analog recovered from engineering bacterial cells according to Example 4 was evaluated by a tibia test. (Parlow, A. F., et al., Endocrinology (1965) 77, 1126.) Rats were hypophysectomized at 28-30 days of age, then kept for 10-14 days without treatment. Bovine growth hormone derived from bovine pituitaries or from recombinant E. coli was dissolved in 0.15M NaCl+0.01 M borate, pH 10.0. Rats (4-7 per group) received daily subcutaneous injections of bGH solutions (5-125 µg/day in 0.2 cc) for 5 days while kept on a normal diet (Purina Rat-Chow and water ad-libitum). The animals were sacrificed on the 6th day, their foreleg knee-bones taken out, cut longitudinally, fixed with acetone and stained with 2% $AgNO_3$. The width of the epiphyseal plates were measured by observation through a dissecting binocular (Nikon). Mean values (of 40 readings per rat) were used for the construction of log dose-response curves. Results are shown in FIG. 5.

EXAMPLE 6

Effect of pRec 2/3 bGH analog on Lactogenesis in Dairy Cows

The lactogenic effect of bGH has been well documented in the scientific literature in the reports of Bines, J. et al, Brit J. Nutri. (1980) 43, 179 and Peel, C. et al, J. Nutr. (1981) 111, 1662. Bauman, D. et al, J. Dairy Sci. Vol. Supp. 1, Abst 86 (1982) reported that milk production was increased by rDNA bGH. An experiment was conducted to determine the effects of pRec 2/3 bGH on lactogenesis in comparison with natural bGH. Eighteen Holstein cows ranging from 141 to 154 days postpartum were randomly assigned to treatment and blocked according to milk production according to the following design.

| Treatment Groups | Pre-treatment Period | Daily GH Injection |
| --- | --- | --- |
| Control | 5 days | Saline |
| Natural bGH | 5 days | 25 mg/day for 10 days |
| pRec ⅔ bGH | 5 days | 25 mg/day for 10 days |

The bGHs were put in solution with 0.1 M $NaHCO_3$ aqueous buffer (pH=8.2) at the concentration of 1 mg/ml immediately prior to each day's injections. The cows were injected with placebo or bGH solution daily for 10 days in a subcutaneous site in the neck region. No injections were given during the 5-day pretreatment period.

The cows were milked twice daily at approximately 6:00 a.m. and 5:00 p.m. Milk weights were recorded by the Boumatic system and recorded in the dairy data system.

The average milk production values for the pre-treatment and bGH treatment periods are shown in Table I. The production level of the control cows was unchanged while the milk volume increased to a similar degree in both the bGH groups. The natural bGH caused an 11.9% increase in milk for a 10-day period and bGH analog treatment resulted in a 10.2% increase.

The data were not analyzed for statistical significance due to the small number of animals, however, the magnitudes of the increases are similar to those reported in the literature.

It was concluded that pRec 2/3 bGH stimulates lactogenesis in dairy cows similar to natural bGH.

TABLE I

Bovine Growth Hormone Effect on Lactogenesis Natural bGH vs pRec ⅔ bGH

| Treatment Group | No. | Av. Daily Milk Production lb/day | | % Increase Over Pretreatment |
|---|---|---|---|---|
| | | Pretreatment 5 days | During GH 10 days | |
| Control | 6 | 57.23 | 57.26 | — |
| Natural bGH 25 mg/day | 5 | 58.54 | 65.50 | 11.9 |
| pRec ⅔ bGH 25 mg/day | 6 | 57.48 | 63.34 | 10.2 |

Each cow was injected subcutaneously with either placebo or bGH solution once daily for 10 days.

EXAMPLE 7

Met-Asp-Gln Porcine Growth Hormone Analog

The construction of pRec pig 24 is shown in FIG. 9 and described in the Description of the Figures. The intermediate plasmids in the construction of pRec pig 24 are shown in FIGS. 6-8 and described in the Description of the Figures.

pRec pig 24 was introduced into *E. coli* strains A2097 and A4255 by transformation. These strains produce upon growth and induction an analog of porcine growth hormone (pGH) having the amino acid sequence Met-Asp-Gln added to the N terminus of the phenylalanine form of natural pGH. The amount of pGH analog produced by these strains was about 10% of the total protein produced by the bacteria as calculated by scanning the pGH band on Coomassie blue stained SDS polyacrylamide gels and determining the total protein by the Biuret modification of the method of Lowry. (E. Layne, Methods in Enzymology 3:450 (1957)).

EXAMPLE 8

Growth of pRec pig 24 in A2097

I. Stock Cultures

Stock cultures of pRec pig 24 were grown on casein hydrolysate medium (see Inoculum), then diluted two-fold with freezing medium and stored at −80° C. Freezing medium contains per 500 ml:

| K$_2$HPO$_4$ | 6.3 g |
|---|---|
| KH$_2$PO$_4$ | 1.8 g |
| Na Citrate | 0.45 g |
| MgSO$_4$.7H$_2$O | 0.09 g |
| (NH$_4$)$_2$SO$_4$ | 0.9 g |
| Glycerol | 44.0 g |

II. Inoculum

The inoculum was propagated in 20 g/l tryptone, 10/l yeast extract, 5 g/l NaCl. Sterile medium in a shake flask was inoculated from stock culture and incubated 15 hours on a shaker at 30° C. and approximately 200 r.p.m. As needed, subsequent stages in inoculum propagation were carried out in stirred aerated fermenters. Sterile medium was inoculated with 2-10% inoculum and incubated 15 hours at 30° C., pH 7±0.5 with agitation and aeration to maintain a dissolved oxygen level above 20% air saturation.

III. Production

The production medium contains:

| Tryptone | 20 g/l |
|---|---|
| Yeast extract | 10 g/l |
| K$_2$HPO$_4$ | 2.5 g/l |
| MgSO$_4$.7H$_2$O | 1 g/l |
| NaCl | 5 g/l |
| Biotin | 0.1 mg/l |
| Thiamine | 1 mg/l |
| Trace elements solution | 3 ml/l |

The medium also contains 100 mg/liter ampicillin. The ampicillin is optional for production but is always found in the medium used for growing the inoculum.

Biotin, thiamine and ampicillin in concentrated solution were filter sterilized separately and added to the sterile production medium before inoculation. Sterile glucose solution was added initially to supply 10 g/l. At the induction step another 10 g/l of glucose was added.

The trace elements solution contains:

| FeCl$_3$ | 27 g |
|---|---|
| ZnCl$_2$.4H$_2$O | 2 g |
| CoCl$_2$.2H$_2$O | 2 g |
| NaMoO$_4$.2H$_2$O | 2 g |
| CaCl$_2$.2H$_2$O | 1 g |
| CuCl$_2$ | 1 g |
| H$_3$BO$_3$ | 0.5 g |
| Conc. HCl | 100 ml |
| Deionized H$_2$O | 900 ml |

The medium is inoculated with 0.5-10% inoculum culture and incubated at 30° C. Agitation-aeration rates are set to maintain a dissolved oxygen level above 20% air saturation.

The pH is maintained at 7±0.2 with NH$_3$. Once cell concentration reaches about 3.5 g/l (OD$_{660}$=10) induction is started.

The temperature is raised to 42° C. and maintained at 42° C. for 2 hours. The culture is then chilled and cells are recovered by centrifugation for hormone purification.

The pGH can then be recovered and purified by the methods described in Example 4 for bGH.

EXAMPLE 9

Growth of pRec pig 24 in *E. coli* A4255

I. Stock Cultures

Stock cultures of pRec pig 24/A4255 were grown on casein hydrolysate medium (see Inoculum), then diluted two-fold with freezing medium and stored at −75° C. Freezing medium contains:

| K$_2$HPO$_4$ | 6.3 g |
|---|---|
| KH$_2$PO$_4$ | 1.8 g |
| Na Citrate | 0.45 g |
| MgSO$_4$.7H$_2$O | 0.09 g |
| (NH$_4$)$_2$SO$_4$ | 0.9 g |
| Glycerol | 44.0 g |
| Deionized H$_2$O | 450 ml |

II. Inoculum

The inoculum was propagated in minimal medium (see below), 10 g/l yeast extract and 2 g/l NaCl. Sterile medium in a shake flask was inoculated from stock culture and incubated 15 hours on a shaker at 30° C. and approximately 250 r.p.m. As needed subsequent stages in inoculum propagation were carried out in stirred aerated fermenters. Sterile medium was inoculated with 2-10% inoculum and incubated 15 hours at 30° C., pH ±0.5 with agitation and aeration to maintain a dissolved oxygen level above 20% air saturation.

Minimal Media

The minimal media standardly used for production purposes with pRec pig 24/A4255 is:

|  | For Fermenters | For Shake Flasks |
|---|---|---|
| $K_2HPO_4$ | 6 g/l | 6 g/l |
| $KH_2PO_4$ | 4 g/l | 4 g/l |
| $NH_4Cl$ | 1 g/l | 1 g/l |
| $MgSO_4.7H_2O$ | 3 g/l | 0.2 g/l |
| 10% $FeNH_4$ Citrate | 0.3 ml/l | 0.1 ml/l |
| Trace Elements Solution | 3 ml/l | 1 ml/l |
| Antifoam, Silicone | 0.5 ml/l | |

Autoclave.

Ampicillin (100 mg/l) may be added to the media. For the shake flasks sterile glucose was added initially to supply 5 g/l. For the fermenters 50% glucose was autoclaved separately and added to 20 gm/l. Additional 50% glucose was fed during the fermentation at a rate of approximately 1.08 gm/glucose per O.D. unit. The pH was controlled by feeding 25% $NH_4$. Antifoam was added as needed. Biotin was added at 3 mg/l in fermenters on 0.5 mg/l in shake flasks. The trace elements solution contains:

|  | g/l |
|---|---|
| $H_3BO_3$ | 0.50 |
| $CuCl_2$ ($CuSO_4.5H_2O$) | 1.0 (1.85) |
| $CaCl_2.2H_2O$ | 3.0 |
| $MnSO_4.H_2O$ | 1.0 |
| $Na_2MoO_4.2H_2O$ | 2.0 |
| $CaCl_2.6H_2O$ | 2.0 |
| $ZnCl_2.4H_2O$ ($ZnSO_4.7H_2O$) | 2.0 (2.78) |
| Concentrated HCl | 100 ml |
| Distilled water | 900 ml |

The compounds in parenthesis are alternate compounds which may be used in place of the compounds preceding them. The parenthesized amounts refer to appropriate amounts of such alternative compounds.

The medium is inoculated with 0.5-10% inoculum culture and incubated at 30° C. Agitation-aeration rates are set to maintain a dissolved oxygen level above 20% air saturation. The pH is maintained at 7±0.2 with $NH_3$. Once cell concentration reaches about 3.5 g/l ($OD_{660}=10$) induction is started.

The temperature is raised to 42° C. and maintained at 42° C. for 15 minutes. Incubation is continued for 120 minutes at 38° C. The culture is then chilled and cells are recovered by centrifugation for hormone purification.

The pGH can then be recovered and purified by the methods described in Example 4 for bGH.

EXAMPLE 10

Met-Porcine Growth Hormone Analog

The construction of p3007 is shown in FIG. 7 and described in the Description of the Figures. The intermediate plasmids in the construction of p3007 are shown in FIGS. 3 and 6 and described in the Description of the Figures.

p3007 was introduced into *E. coli* strain A1645 by transformation. This strain produces upon growth and induction an analog of porcine growth hormone (pGH) having the amino acid methionine added to the N terminus of the phenylalanine form of natural pGH (met-pGH). The amount of pGH analog produced by this strain was about 10% of the total protein produced by the bacteria as calculated by scanning the pGH band on Coomassie blue stained SDS polyacrylamide gels and determining the total protein by the Biuret modification of the method of Lowry. (E. Layne, Methods in Enzymology 3:450 (1957)).

EXAMPLE 11

Growth of p3007 in A1645

I. Stock Cultures

Stock cultures of p3007 were grown on casein medium (see Inoculum), then diluted two-fold with freezing medium and stored at −80° C. Freezing medium contains per 500 ml:

| | |
|---|---|
| $K_2HPO_4$ | 6.3 g |
| $KH_2PO_4$ | 1.8 g |
| Na Citrate | 0.45 g |
| $MgSO_4.7H_2O$ | 0.09 g |
| $(NH_4)_2SO_4$ | 0.9 g |
| Glycerol | 44.0 g |

II. Inoculum

The inoculum was propagated in 20 g/l tryptone, 10 g/l yeast extract and 5 g/l NaCl. Sterile medium in a shake flask was inoculated from stock culture and incubated 15 hours on a shaker at 30° C. and approximately 200 r.p.m. As needed subsequent stages in inoculum propagation were carried out in stirred aerated fermenters. Sterile medium was inoculated with 2-10% inoculum and incubated 15 hours at 30° C., pH 7±0.5 with agitation and aeration to maintain a dissolved oxygen level above 20% air saturation.

III. Production

The production medium contains:

| | |
|---|---|
| Tryptone | 20 g/l |
| Yeast extract | 10 g/l |
| $K_2HPO_4$ | 2.5 g/l |
| $MgSO_4.7H_2O$ | 1 g/l |
| NaCl | 5 g/l |
| Biotin | 0.1 mg/l |
| Thiamine | 1 mg/l |
| Trace elements solution | 3 ml/l |

The medium also contains 100 mg/liter ampicillin. The ampicillin is optional for production but is always found in the medium used for growing the inoculum.

Biotin, thiamine and ampicillin in concentrated solution were filter sterilized separately and added to the sterile production medium before inoculation. Sterile glucose solution was added initially to supply 10 g/l. At the induction step another 10 g/l of glucose was added. The trace elements solution contains:

| | |
|---|---|
| $FeCl_3$ | 27 g |
| $ZnCl_2.4H_2O$ | 2 g |
| $CoCl_2.2H_2O$ | 2 g |
| $NaMoO_4.2H_2O$ | 2 g |
| $CaCl_2.2H_2O$ | 1 g |
| $CuCl_2$ | 1 g |
| $H_3BO_3$ | 0.5 g |
| Conc. HCl | 100 ml |
| Deionized $H_2O$ | 900 ml |

The medium is inoculated with 0.5–10% inoculum culture and incubated at 30° C. Agitation-aeration rates are set to maintain a dissolved oxygen level above 20% air saturation. The pH is maintained at 7±0.2 with $NH_3$. Once cell concentration reaches about 3.5 g/l ($OD_{660}=10$) induction is started.

The temperature is raised to 42° C. and maintained at 42° C. for 2 hours. The culture is then chilled and cells are recovered by centrifugation for hormone purification.

The pGH can then be recovered and purified by the methods described in Example 4 for bGH.

EXAMPLE 12

Activity of Met pGH Analog Produced by p3007 in A1645

1. Radioimmunoassay comparison of Met pGH analog with natural pGH

A solution containing 100 ng/ml met pGH analog was prepared in phosphate buffered saline (1% BSA). This solution was diluted serially to concentrations of 50, 25, 12.5, 6.25, 3.12, 1.56 and 0.78 ng/l. Duplicate 0.1 ml aliquots of these solutions were submitted to RIA using a double antibody procedure. The dilution curve was comparable to that obtained with natural pGH.

2. Radioreceptor Binding Assay

A radioreceptor binding assay was performed with rabbit liver membranes as described by T. Tushima and H.G. Freisen (Y. Chin., Endocr. Metab. 37, 334 (1973)) using $^{125}I$-bGH as the tracer and authentic pGH solutions for the construction of calibration curves. Samples were incubated in triplicate for two hours at room temperature in 0.3 ml of assay buffer (50 mM Tris, 15 mM $CaCl_2$ and 5 mg/ml bovine serum albumin, pH 7.6). The tubes contained $^{125}I$-bGH (20,000 cpm of preparation of 30–60 uci/ug), 150–250 ug liver membrane protein and either natural pGH (1–100 ng) or extracts of met pGH. The result demonstrated that the pGH activity of the met pGH analog is comparable to that of natural pGH.

3. Procedure for Radioreceptor Binding Assay of Met Porcine Growth Hormone Analog A. Preparation of Liver Membranes Fresh liver of pregnant (3rd trimester) rabbit is washed with saline, cut into small pieces and then homogenized for 1 minute at 4° C. on low speed in a Waring blender, using 2 ml/g of 0.3 M sucrose containing 10 M p-methyl-sulfonylfluoride (PMSF). The homogenate is filtered through 4 layers of cheese-cloth and spun at 1,000 Xg for 10 minutes.

The pellet is resuspended in 1 ml/g of sucrose solution and spun again. The two supernatants are combined and spun at 20,000 Xg for 20 minutes. The membrane pellet is resuspended ml/g liver of 0.15 M KCl, 10 M PMSF and spun again at 20,000 Xg for 20 minutes. The pellet is now homogenized in 1 ml/g liver of distilled water, using 4 strokes in a loose-fitting Dounce homogenizer. This homogenate is first spun for 10 minutes at 1,000 Xg, then the supernatant is centrifuged at 20,000 Xg for 20 minutes, resulting in a final membrane pellet. This pellet is resuspended in volume water to 1 volume pellet, and 1 ml portions are put into storage at −20° C. or lower.

B. Iodination of pGH

Pure authentic pGH is iodinated by conventional methods, using the Bolton-Hunter reagent, then separated by gel-filtration on Sepadex G25.

C. Assay Procedure

All dilutions are performed in binding buffer (25 mM Tris, 10 mM and 5 mg/ml bovine serum albumin, pH 7.4–7.6). Assay is performed in 10×75 mm polystyrene tubes. Each tube contains:

0.1 ml of $^{125}I$ bGH solution (approximately 10,000 cpm).

0.1 ml of a known solution of authentic pGH, or unknown sample.

0.1 ml of membrane solution (stock from freezer, diluted with 2 volumes of buffer).

Care is taken to continuously stir the membrane preparation during precipitation to avoid settling of the particles.

The concentration of the standard solutions of authentic pGH should range from 10 to 1,000 ng/ml. Assay is routinely run in triplicate. The tubes are incubated with shaking at room temperature for 2 hours, then 1.5 ml cold binding buffer is added to each tube, and they are spun for 20 minutes at 3,000 RPM. The supernatant is removed quickly by suction and the tubes with the membrane pellets taken for gamma-counting.

A calibration curve is constructed by plotting the values of radioactivity found for the standard samples against concentrate and the activity of growth hormone in the unknown samples is calculated by comparison.

EXAMPLE 13

Activity of Met-Asp-Gln pGH Analog Produced by pRec pig 24

1. Radioimmunassay Comparison of Met-Asp-Gln-pGH Analog with met-pGH Analog

A solution containing 250 ng/50 ul met-asp-gln pGH analog was prepared in RIA buffer (pH 8.5). This solution was diluted serially to concentrations of 125, 62.5, 31.25, 15.6, 7.8, 3.9, 1.9, and 0.9 ng/50 ul. Duplicate 50 ul aliquots of these solutions were submitted to RIA using crude Protein A in place of a second antibody. The dilution curve was comparable to that obtained with met pGH.

RIA buffer, sodium barbital - 50 nM, NaCl - 150 nM, EDTA - 10 nM, Triton x-100 - 0.05%, BSA - 1%, SDS - 0.2%

2. Radioreceptor Binding Assay

A radioreceptor binding assay was performed with rabbit liver membranes as described by T. Tushima and H.G. Freisen (Y. Chin., Endocr. Metab. (1973) 37, 334)

using $^{125}$I bGH as the tracer and met-pGH analog solutions for the construction of calibration curves. Samples were incubated in triplicate for two hours at room temperature in 0.3 ml of assay buffer (50 mM Tris, 15 mM CaCl$_2$ and 5 mg/ml bovine serum albumin, pH 7.6). The tubes contained $^{125}$I bGH (30,000 cpm/100 ul), 150-250 ug liver membrane protein and either met pGH analog (1-1000 ng) or extracts of met-asp-gln pGH analog. The result demonstrated that the pGH activity of the met-asp-gln pGH analog is comparable to that of met-pGH which has previously been shown to be comparable to natural pGH (See Example 12).

EXAMPLE 14

Biological Activity of the Met-Asp-Gln-PGH and met-pGH Analogs

A recent study (C. A. Spence et al., Abstract entitled "Effect of Exogenous Growth Hormone On Fetal Energy Storage and Lactation Performance in Sows," from The Annual Meeting of The American Society of Animal Science, Univ. of Missouri, Aug. 7-10, 1984) indicate that administration of pituitary-derived porcine growth hormone increases sow lactation and piglet litter survival. In studies of lactation performance, administration of the met-asp-gln pGH analog or the met-pGH analog to pregnant sows improved sow lactation and piglet litter survival.

What is claimed is:

1. A plasmid for production of met porcine growth hormone or met-asp-gln porcine growth hormone which upon introduction into an *Escherichia coli* host cell containing the thermolabile repressor C$_I$ renders the host cell capable, upon increasing the temperature of the host cell to a temperature at which the repressor is inactivated, of effecting expression of DNA encoding the met porcine growth hormone or met-asp-gln procine growth hormone, such expression resulting in the production of the met porcine growth hormone or met-asp-gln procine growth hormone, the plasmid comprising a double-stranded DNA molecule which comprises in 5' to 3' order the following:
   1) a DNA sequence which contains the promotor and operator P$_L$O$_L$ from λ bacteriophage;
   (2) an N utilization site for binding antiterminator N protein produced by the *Escherichia coli* host cell;
   3) a DNA sequence containing the mutant C$_{II}$ ribosomal binding site from λ bacteriophage having the sequence:

TAAGGAAGTACTTACAT

ATTCCTTCATGAATGTA;

4) an ATG initiation codon;
   5) DNA encoding the met porcine growth hormone or met-asp-gln procine growth hormone;
   and which additionally includes a DNA sequence which contains an origin of replication from the bacterial plasmid pBR322 capable of autonomous replication in the *Escherichia coli* host cell and a DNA sequence which contains a gene encoding a selectable or identifiable phenotypic trait which is manifested when the plasmid is present in the host cell.

2. A circular, closed plasmid of claim 1.

3. A plasmid of claim 1, wherein the phenotypic trait is drug resistance or temperature sensitivity.

4. A plasmid of claim 3, wherein the drug resistance is resistance to ampicillin, chloramphenicol or tetracycline.

5. A host plasmid system comprising the plasmid of claim 1 in an *Escherichia coli* host.

6. A method for producing met porcine growth hormone or met-asp-gln procine growth hormone which comprises growing a host plasmid system of claim 5 under conditions permitting production of the met procine growth hormone or met-asp-gln procine growth hormone and recovering the met porcine growth hormone or met-asp-gln procine growth hormone so produced.

7. A method of claim 6, wherein the conditions comprise growth of the host plasmid system for an initial period of time at about 30° C., and then for an additional period of time at 42° C., said growth being carried out on a minimal medium.

8. A method of claim 7, wherein the additional period of time is about 2 hours.

9. A method of claim 6, wherein the conditions comprise growth of the host plasmid system for an initial period of time at 30° C., followed by growth for a second period of time at 42°·C., followed by growth for a third period of time at 38° C., said growth being carried out on a casein hydrolysate medium.

10. A method of claim 9, wherein the second period of time is about 15 minutes and the third period of time is about 2 hours.

11. A plasmid designated pRec pig 24 and deposited in *Escherichia coli* under ATTCC Accession No. 53433.

12. A plasmid designated p6200 and deposited in *Escherichia coli* under ATCC Accession No. 39980.

* * * * *